US008486370B2

United States Patent
Carpenter et al.

(10) Patent No.: US 8,486,370 B2
(45) Date of Patent: Jul. 16, 2013

(54) HETEROCYCLIC LIGANDS FOR INTEGRIN IMAGING AND THERAPY

(75) Inventors: Richard D. Carpenter, Suisun City, CA (US); Mirela Andrei, Ploiesti (RO); Ruiwu Liu, Sacramento, CA (US); Kit S. Lam, Davis, CA (US); Mark J. Kurth, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 518 days.

(21) Appl. No.: 12/440,219

(22) PCT Filed: Sep. 7, 2007

(86) PCT No.: PCT/US2007/077860
§ 371 (c)(1),
(2), (4) Date: Aug. 18, 2010

(87) PCT Pub. No.: WO2008/031016
PCT Pub. Date: Mar. 13, 2008

(65) Prior Publication Data
US 2010/0310455 A1    Dec. 9, 2010

Related U.S. Application Data

(60) Provisional application No. 60/843,284, filed on Sep. 8, 2006.

(51) Int. Cl.
*A61K 51/00* (2006.01)
(52) U.S. Cl.
USPC ........................................................ 424/1.69
(58) Field of Classification Search
USPC ........................................................ 424/1.69
See application file for complete search history.

(56) References Cited

U.S. PATENT DOCUMENTS
7,576,175 B2   8/2009 Lam et al.

FOREIGN PATENT DOCUMENTS
WO        WO 01/58871 A1 *  8/2001

OTHER PUBLICATIONS

Carpenter et al., J. Comb. Chem., 2006, 8, 907-914.
Chen et al., Biochemistry, 1998, 37:8743-8753.
Lin et al., J. Med. Chem., 1999, 42:920-934.
Park et al., Letters Pept. Sci., 8:171-178, 2002.
International Search Report mailed on Aug. 18, 2008, for International Application No. PCT/US2007/077860, filed on Sep. 7, 2007, 2 pages.
Peng, Li et al., "Combinatorial chemistry indentifies high-affinity peptidomimetics against $\alpha_4\beta_1$ integrin for in vivo tumor imaging," Nature Chemical Biology, Jul. 2006, vol. 2, No. 7, pp. 381-389.

* cited by examiner

Primary Examiner — Brandon Fetterolf
Assistant Examiner — Christopher R Stone
(74) Attorney, Agent, or Firm — Kilpatrick, Townsend & Stockton LLP

(57) ABSTRACT

The present invention provides $\alpha_4\beta_1$ integrin ligands that display high binding affinity, specificity, and stability. The ligands comprise a peptide having n independently selected amino acids, wherein at least one amino acid is an unnatural amino acid or a D-amino acid, and wherein n is an integer of from 3 to 20. Methods are provided for administering the ligands for treating cancer, inflammatory diseases, and autoimmune diseases. Also provided are methods for administering the ligands for imaging a tumor, organ, or tissue in a subject.

49 Claims, 20 Drawing Sheets

LLP2A

*Scheme 1.* Synthesis of KLCA analogs (a) (Cl)$_2$C=S, Et$_3$N, EtOAc;

(b) 5-R$^2$-4-R$^3$-2-XH-anilines, CH$_2$Cl$_2$, 16 h, then DIC or EDC;

(c) swell/DMF, 3h;

(d) 20% piperidine/DMF;

(e) Fmoc-Ach-OH, DIC, HOBt, DMF; (d);

(f). Fmoc-Aad(O*t*Bu)-OH, DIC, HOBt, DMF; (d).;

(g) Dde-K(Fmoc)-OH, DIC, HOBt, DMF; (d);

(h) (*E*)-3-(pyridin-3-yl)acrylic acid, DIC, HOBt, DMF;

(i) 2% H$_2$NNH$_2$/DMF;

(j) 3-20 or 21 HBTU, EtN(*i*Pr)$_2$, DMF;

(k) TFA, (*i*Pr)$_3$SiH, H$_2$O.

*Scheme 2.* Preparation of KLCA14-Cy5.5 Dye (a) swell, DMF, 24 h.;

(b) 20% piperidine/DMF;

(c) Fmoc-K(Dde)-OH, DIC, OBt, DMF; (b);

(d) Fmoc-NH-linker-CO$_2$H, DIC, HOBt, DMF; (b); (d); (b);

(e) Fmoc-Ach-OH, DIC, HOBt, DMF; b.;

(f) Fmoc-Aad(O*t*Bu)-OH, DIC, HOBt, DMF; (b);

(g). Fmoc-K(Alloc)-OH, DIC, HOBt, DMF; (b);

(h) 14, HBTU, DIEA, DMF; Pd(PPh$_3$)$_4$, PhSiH$_3$, DMF;

(i) (*E*)-3-(pyridin-3-yl)acrylic acid, DIC, HOBt, DMF;

(j) 2% H$_2$NNH$_2$/DMF;

(k) Cy5.5-NHS, DIEA, DMF;

(l) TFA, H$_2$O, (*i*Pr)$_3$SiH.

1: IC$_{50}$ = 37.2 ± 24.3 pM

2: IC$_{50}$ = 185.6 ± 74.79 nM

3: IC$_{50}$ = 444 ± 26.8 nM

4: IC$_{50}$ = 340 ± 23.33 nM

5: IC$_{50}$ = 305 ± 58 pM

6: IC$_{50}$ = 344 ± 266 nM

7: IC$_{50}$ = 419.5 ± 333 nM

8: IC$_{50}$ = 655 ± 79 nM

9: IC$_{50}$ = 27.5 ±1.76 nM

10: IC$_{50}$ = 379 ± 138.5 nM

Cell Adhesion Assay Graphs and IC$_{50}$ Values

Cy5.5 Dye Xenograft Murian Images

*In-vivo*

Dose: 1 nmol of LLP2A-Cy5.5

Left Limb Tumor Cell Line: A549

Right Limb Tumor Cell Lines: Molt4 and Raji

Time Point *i.v.* Post-Injection: 24 h

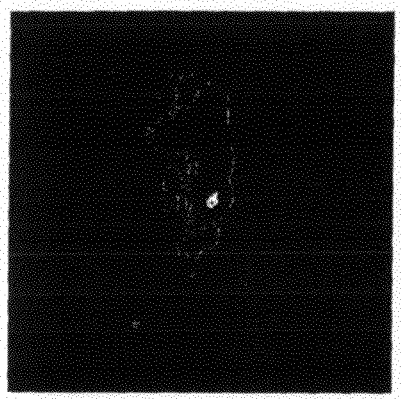

*In-vivo*

Dose: 10 nmol of KLCA14-Cy5.5

Left Limb Tumor Cell Line: A549

Right Limb Tumor Cell Lines: Molt4 and Raji

Time Point *i.v.* Post-Injection: 5 min

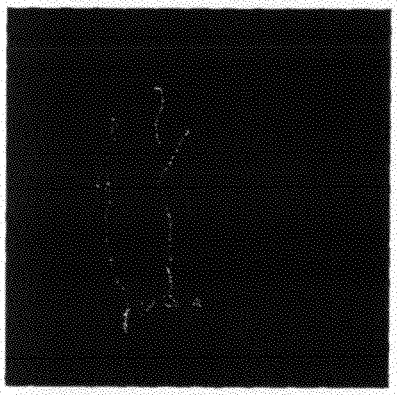

*In-vivo*

Dose: 10 nmol of KLCA14-Cy5.5

Left Limb Tumor Cell Line: A549

Right Limb Tumor Cell Lines: Molt4 and Raji

Time Point *i.v.* Post-Injection: 4 h

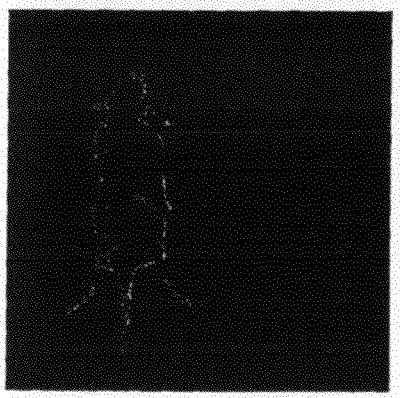

Figure 6B

*Ex-Vivo*
Dose: 10 nmol of KLCA14-Cy5.5
Top from left to right: Molt-4 tumor, Raji, tumor, lung, bladder, spleen, prostate, testis, lymphnodes.
Bottom from left to right: A549 tumor, liver, kidney, heart, intestine, muscle, skin.
Time Point *i.v.* Post-Injection: 24 h

*In-vivo*
Dose: 10 nmol of KLCA14-Cy5.5
Left Limb Tumor Cell Line: A549
Right Limb Tumor Cell Lines: Molt4 and Raji
Time Point *i.v.* Post-Injection: 24 h

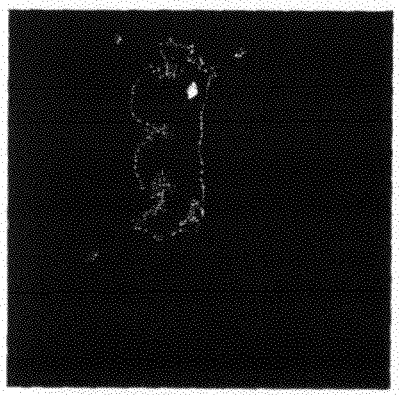

*In-vivo*
Dose: 10 nmol of KLCA14-Cy5.5
Left Limb Tumor Cell Line: A549
Right Limb Tumor Cell Lines: Molt4 and Raji
Time Point *i.v.* Post-Injection: 72 h

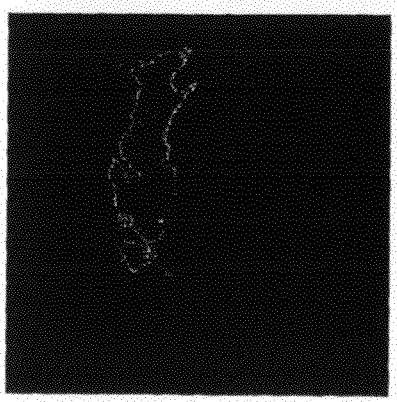

HETEROCYCLIC LIGANDS FOR INTEGRIN IMAGING AND THERAPY

CROSS-REFERENCES TO RELATED APPLICATIONS

This application claims priority to U.S. Provisional Application No. 60/843,284, filed Sep. 8, 2006, which is incorporated herein by reference, in its entirety.

STATEMENT AS TO RIGHTS TO INVENTIONS MADE UNDER FEDERALLY SPONSORED RESEARCH OR DEVELOPMENT

This invention was made with support from the U.S. Government under Grant (or Contract) No. CA 113298, awarded by the National Institutes of Health. The Government has certain rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Cell adhesion is a process by which cells associate with each other, migrate towards a specific target, or localize within the extracellular matrix. Cell adhesion constitutes one of the fundamental mechanisms underlying numerous biological phenomena. For example, cell adhesion is responsible for the adhesion of hematopoietic cells to endothelial cells and the subsequent migration of those hematopoietic cells out of blood vessels and to the site of injury. As such, cell adhesion plays a role in pathologies such as inflammation, autoimmune disease, and tumor metastasis in mammals.

Investigations into the molecular basis for cell adhesion have revealed that various cell surface macromolecules, collectively known as cell adhesion molecules or receptors, mediate cell-cell and cell-matrix interactions. For example, members of the integrin family of cell surface receptors mediate cell-cell and cell-matrix interactions and regulate cell motility, migration, survival, and proliferation (Hynes, *Cell,* 69:11-25 (1992); Hynes, *Cell,* 110:673-687 (2002)). Integrins are non-covalent heterodimeric complexes consisting of two subunits, α and β. There are at least 18 different α subunits and at least 8 different β subunits.

Integrins are implicated in a variety of diseases and disorders, such as cancer, inflammation, autoimmune diseases, and genetic diseases. For example, $\alpha_5\beta_1$, $\alpha_v\beta_3$, and $\alpha_v\beta_5$ integrins play critical roles in promoting tumor metastasis and angiogenesis (Hood and Cheresh, *Nat. Rev. Cancer,* 2:91-100 (2002); Jin and Varner, *Brit. J. Cancer,* 90:561-565 (2004)). In addition, $\alpha_4\beta_1$ integrin is involved in various developmental, physiological, and pathological processes.

$\alpha_4\beta_1$ integrin, also known as very late antigen-4 (VLA-4) or CD49d/CD29, is a leukocyte cell surface receptor that participates in a wide variety of both cell-cell and cell-matrix adhesive interactions (Hemler, *Ann. Rev. Immunol.,* 8:365 (1990)). $\alpha_4\beta_1$ integrin is implicated in metastasis (Holzmann et al., *Curr. Top. Microbio. Immunol.,* 231:125-141 (1998)), regulates leukocyte trafficking, and plays a critical role in inflammation and autoimmune diseases (Yusuf-Makagiansar et al., *Med. Res. Reviews,* 22:146-167 (2002)). For example, $\alpha_4\beta_1$ integrin promotes tumor cell dissemination in distal organs by strengthening their adhesion to the vascular endothelium and facilitating their extravasation (Holzmann et al., id; Hauzenberger et al., *Int. J. Cancer,* 72:1034-1044 (1997)). In chronic lymphocytic leukemia (CLL), $\alpha_4\beta_1$ integrin expression correlates with the presence of lymphadenopathy and determines the entry of the leukemia cells into nodes (Vincent et al., *Blood,* 87:4780-4788 (1996); Till et al., *Blood,* 15:2977-2984 (2002)).

Natural ligands for $\alpha_4\beta_1$ integrin include vascular cell adhesion molecule-1 (VCAM-1) and fibronectin (FN). $\alpha_4\beta_1$ integrin recognizes the primary amino acid sequence Gln-Ile-Asp-Ser (QIDS) in VCAM-1 and Ile-Leu-Asp-Val (ILDV) in FN. Blocking $\alpha_4\beta_1$ interaction with its ligands has been used as a therapeutic strategy for inflammation and autoimmune diseases. For example, monoclonal antibodies to $\alpha_4\beta_1$ integrin have been widely studied for their therapeutic effects. However, there are disadvantages using monoclonal antibody-based therapy due to factors such as low relative efficacy/safety ratios, especially in terms of systemic administration and immunogenic potential. To overcome these disadvantages, derivatives of the ILDV or QIDS sequence in the form of peptide, peptidomimetic, and small molecule non-peptide analogs are of particular interest (Helena et al., id).

By screening a random peptide library with an intact Jurkat T-leukemia cell line, the amino acid sequence Leu-Asp-Ile (LDI) was identified as a unique motif that binds preferentially to $\alpha_4\beta_1$ integrin receptors on human lymphoid malignant cells and not to normal human peripheral lymphocytes (Park et al., *Lett. Pept. Sci.,* 8:171-178 (2002)). The LDI peptide motif also binds preferentially to fresh leukemia cells isolated from patients with acute lymphocytic leukemia. As such, the activated form of a $\alpha_4\beta_1$ integrin is an attractive therapeutic or imaging target for human lymphoid malignancies, e.g., non-Hodgkins lymphoma, acute lymphocytic leukemia, and chronic lymphocytic leukemia, or for other cancers that over-express $\alpha_4\beta_1$ integrin.

By using the ILDV sequence in FN as the starting point for inhibitor design, a series of $\alpha_4\beta_1$ integrin inhibitors were developed (Chen et al., *Biochem.,* 37:8743-8753 (1998)). One of the inhibitors, BIO-1211, was generated by substituting the Ile in ILDV with a 4-((N'-2-methylphenyl)ureido)-phenylacetyl N-terminal cap and adding a Pro (P) residue at the C-terminus. BIO-1211 is a potent $\alpha_4\beta_1$ integrin inhibitor and selectively binds to the activated form of the receptor (Lin et al., *J. Med. Chem.,* 42:920-934 (1999)). However, all of the $\alpha_4\beta_1$ integrin inhibitors to date, including BIO-1211, have been designed as specific therapy for inflammatory and autoimmune diseases, and not for cancer. Further, these $\alpha_4\beta_1$ integrin inhibitors suffer from the significant disadvantage of being susceptible to proteolysis by proteases found, for example, in plasma, the gastrointestinal tract, and tumor cells.

Recently, one-bead one-compound (OBOC) combinatorial library methods were used and the discovery of the bisaryl urea peptidomimetics were identified (see 1, LLP2A; see FIG. 1) as highly potent and selective ligands for the activated form of $\alpha_4\beta_1$ integrin. Additionally, 1, when appropriately radioconjugated (DOTA/$^{64}$Cu or $^{90}$Y), was shown to exhibit excellent potential as a diagnostic or therapeutic agent. Despite the attractive properties of 1, by itself it is not very water soluble. Furthermore, in vivo optical and radioimaging studies in a xenograft model showed rather high uptake in the kidneys, a pharmacokinetic issue which may stem from physiological solubility.

Thus, there is a need to develop $\alpha_4\beta_1$ integrin inhibitors that (1) bind to a $\alpha_4\beta_1$ integrin with high specificity and affinity; (2) bind with high specificity and affinity to tumor cells (e.g., leukemia cells); (3) are more resistant to cleavage or degradation from proteases found, for example, in plasma, the gastrointestinal tract, and tumor cells; and (4) possess suitable water solubility for formulation into therapeutic or imaging compositions. The present invention satisfies this and other needs.

BRIEF SUMMARY OF THE INVENTION

The present invention provides novel heterocyclic a $\alpha_4\beta_1$ integrin ligands (i.e., inhibitors) that advantageously display high binding affinity, specificity, and stability. These ligands are particularly useful for imaging a tumor, organ, or tissue and for treating cancer, inflammatory diseases, and autoimmune diseases. Kits containing these ligands for imaging or therapy are also provided.

As such, in one aspect, the present invention provides compounds having formula I(a) or I(b):

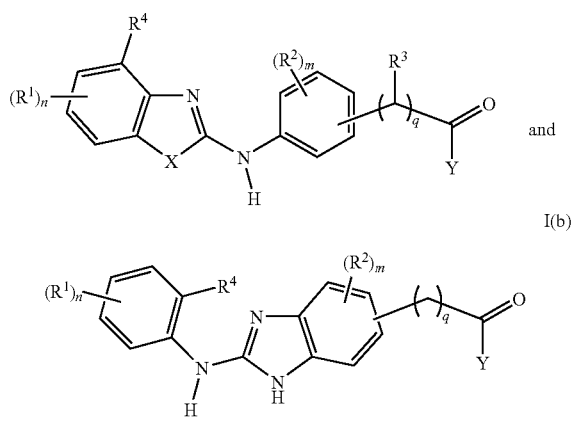

wherein the subscripts n, m and q are each independently selected integers of from 0 to 2; $R^1$ is selected from the group consisting of hydrogen, halogen, $C_1$-$C_4$ alkyl, $C_1$-$C_4$ alkoxy, and $C_1$-$C_4$ haloalkyl; $R^2$ is selected from the group consisting of hydrogen, halogen, $C_1$-$C_4$ alkyl and $C_1$-$C_4$ alkoxy; $R^3$ is selected from the group consisting of hydrogen, $C_1$-$C_4$ alkyl and $C_3$-$C_8$ cycloalkyl; $R^4$ is H or $CH_3$; X is S, O or NH; Y is a peptide having r independently selected amino acids, wherein at least one amino acid is selected from the group consisting of an unnatural amino acid and a D-amino acid; and r is an integer of from 3 to 20.

In one embodiment, Y is a tetrapeptide having the following structure:

$$-Y^1-Y^2-Y^3-Y^4,$$

wherein $Y^1$ is selected from the group consisting of a hydrophobic amino acid and derivatives of lysine, ornithine (Orn) and α,γ-diaminobutyric acid (Dbu); $Y^2$ is a negatively charged amino acid; $Y^3$ is a hydrophobic amino acid; and $Y^4$ is selected from the group consisting of a naturally-occurring amino acid, an unnatural amino acid, and a D-amino acid. In one group of embodiments, $Y^4$ has a carboxyl-terminal group selected from an amide group and a carboxylic acid group.

In another embodiment, Y is a tripeptide having the following structure:

$$-Y^1-Y^2-Y^3,$$

wherein $Y^1$ is selected from the group consisting of a hydrophobic amino acid and derivatives of lysine, ornithine (Orn) and α,γ-diaminobutyric acid (Dbu); $Y^2$ is a negatively charged amino acid; and $Y^3$ is a hydrophobic amino acid.

In another aspect, the present invention provides conjugates having formula II(a) or II(b):

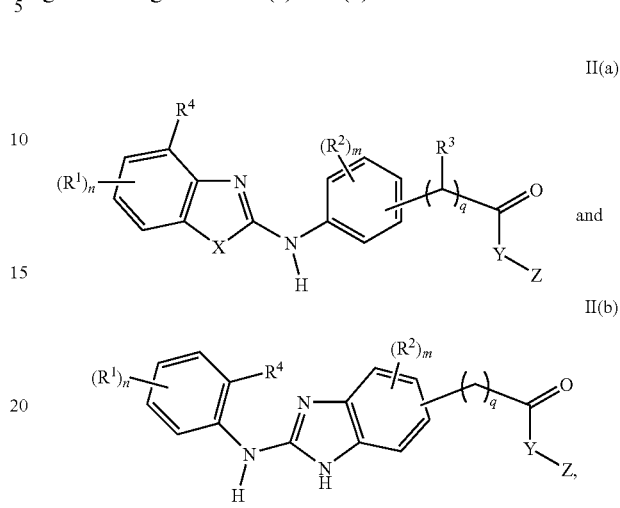

wherein the subscripts n, m and q are each independently selected integers of from 0 to 2; $R^1$ is selected from the group consisting of hydrogen, halogen, $C_1$-$C_4$ alkyl, $C_1$-$C_4$ alkoxy, and $C_1$-$C_4$ haloalkyl; $R^2$ is selected from the group consisting of hydrogen, halogen, $C_1$-$C_4$ alkyl and $C_1$-$C_4$ alkoxy; $R^3$ is selected from the group consisting of hydrogen, $C_1$-$C_4$ alkyl and $C_3$-$C_8$ cycloalkyl; $R^4$ is H or $CH_3$; X is S, O or NH; Y is a peptide having r independently selected amino acids, wherein at least one amino acid is selected from the group consisting of an unnatural amino acid and a D-amino acid; Z is a radionuclide, biotin, a fluorophore, an antibody, horseradish peroxidase, alkaline phosphatase, a chelating agent or a chelating agent-linker conjugate; and r is an integer of from 3 to 20.

In another aspect, the present invention provides a method for treating cancer in a subject in need thereof, the method comprising:

administering to the subject a therapeutically effective amount of a compound having formula II(a) or II(b), as provided above.

In yet another aspect, the present invention provides a method for imaging a tumor, organ, or tissue, the method comprising:

(a) administering to a subject in need of such imaging, a compound having the formula II(a) or II(b):

In still yet another aspect, the present invention provides a method for treating an inflammatory or autoimmune disease in a subject in need thereof, the method comprising administering to the subject a therapeutically effective amount of a compound having the formula I(a) or I(b) as provided above.

In a further aspect, the present invention provides kits for imaging a tumor, organ, or tissue or for treating cancer, an inflammatory disease, or an autoimmune disease comprising one or more of the above-described compounds and directions for use in imaging or therapy.

Other objects, features, and advantages of the present invention will be apparent to one of skill in the art from the following detailed description and figures.

BRIEF DESCRIPTION OF THE DRAWINGS

FIGS. 6A-6B provide xenograph murian images for methods using the conjugates of the invention.

DETAILED DESCRIPTION OF THE INVENTION

I. Definitions

Figure 1:
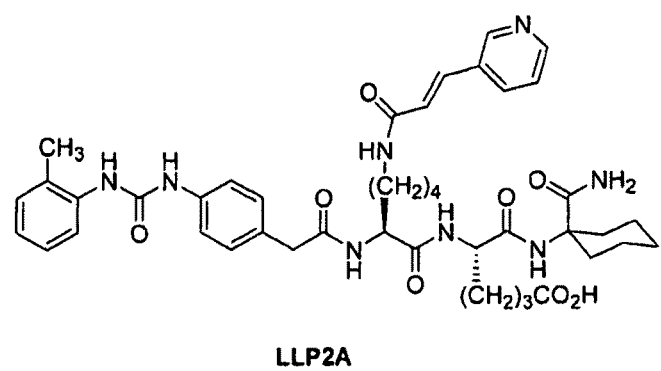
FIG. 1 provides the structure of LLP2A.
Figure 2A:
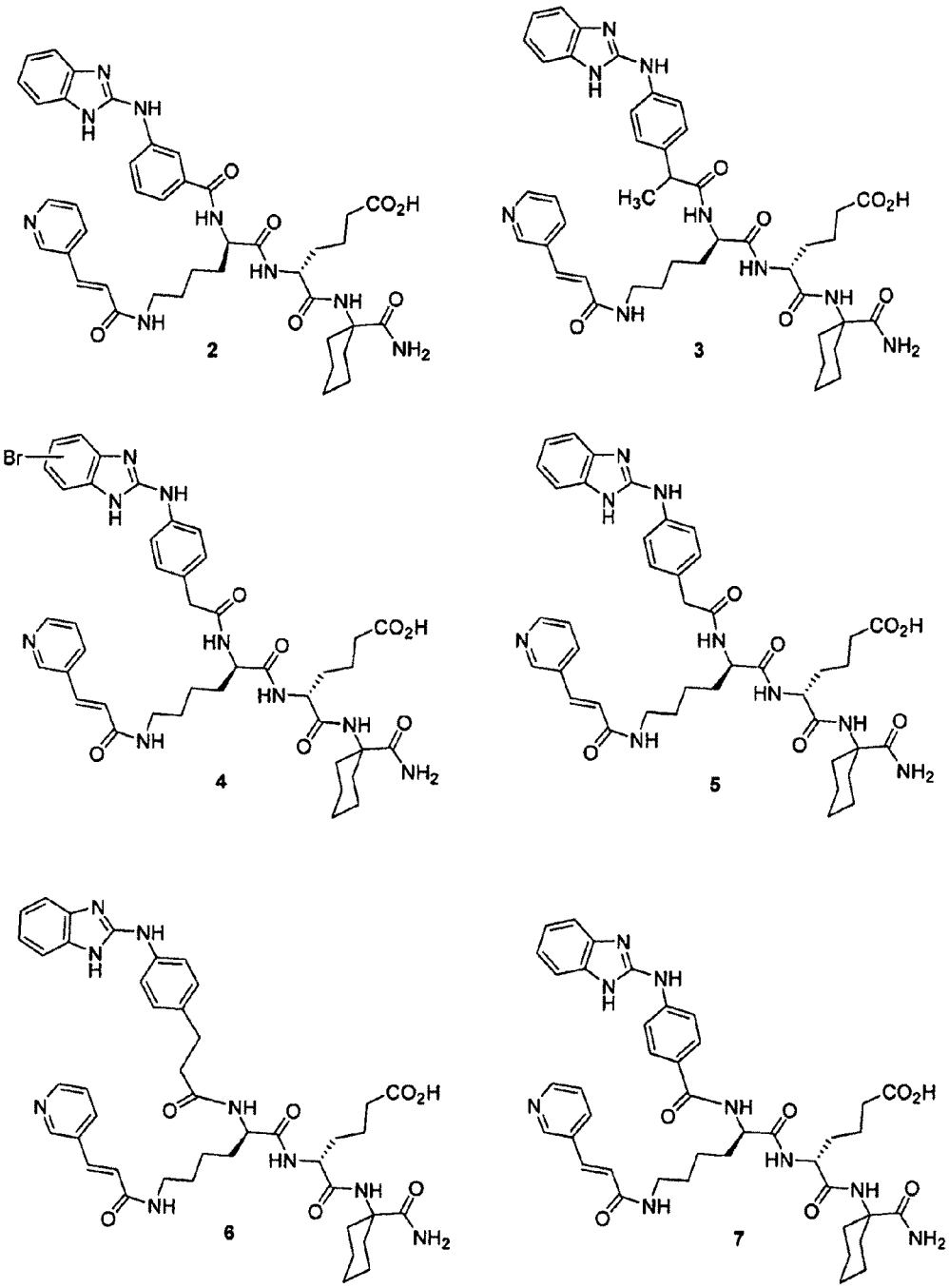
FIGS. 2A-2D provide the structures of compounds and conjugates of the present invention.
Figure 2B:
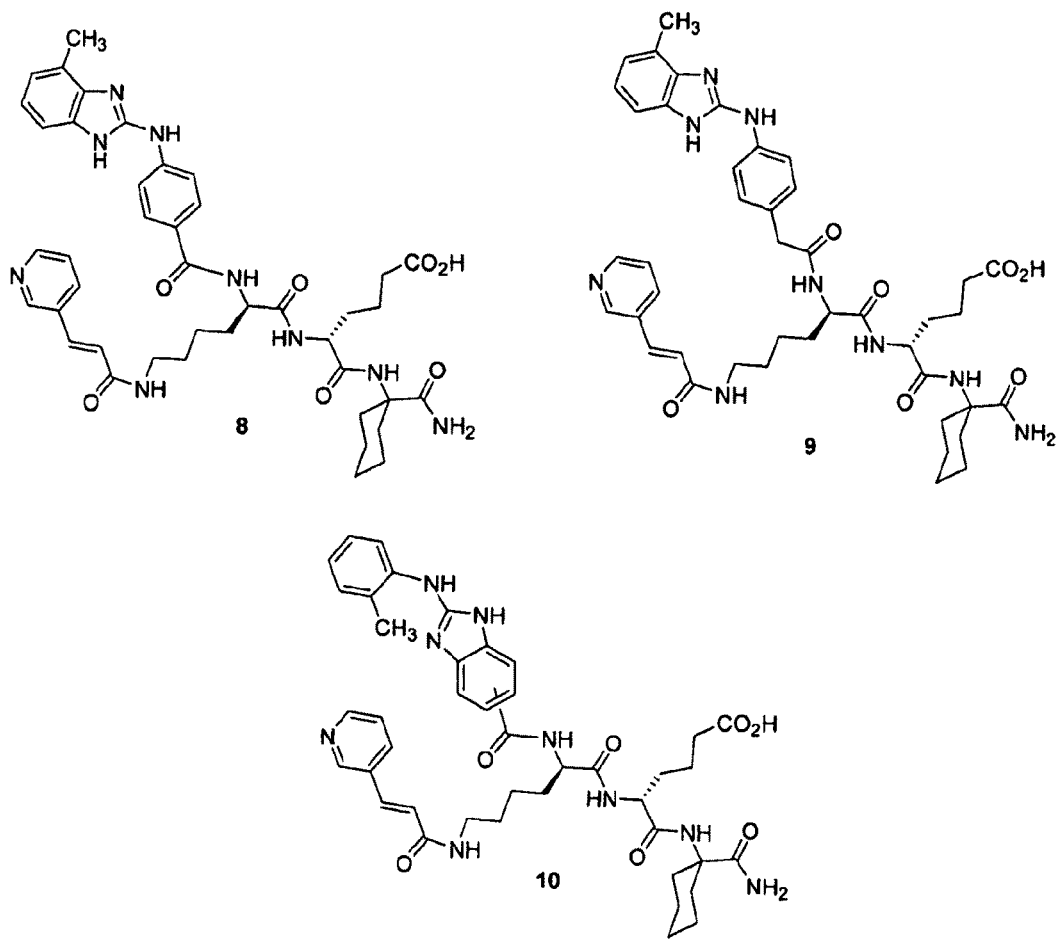
Figure 2C:
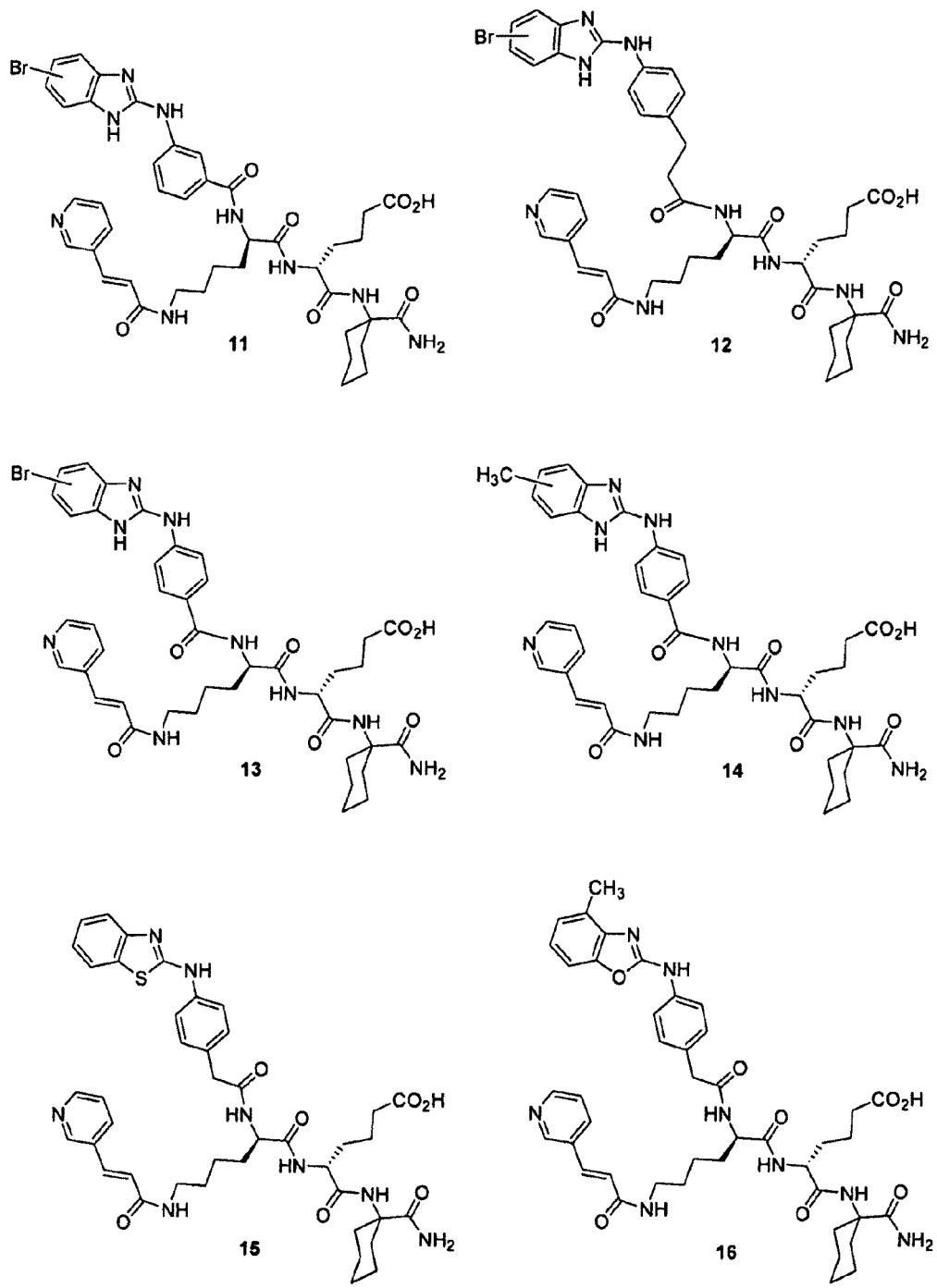
Figure 2D:
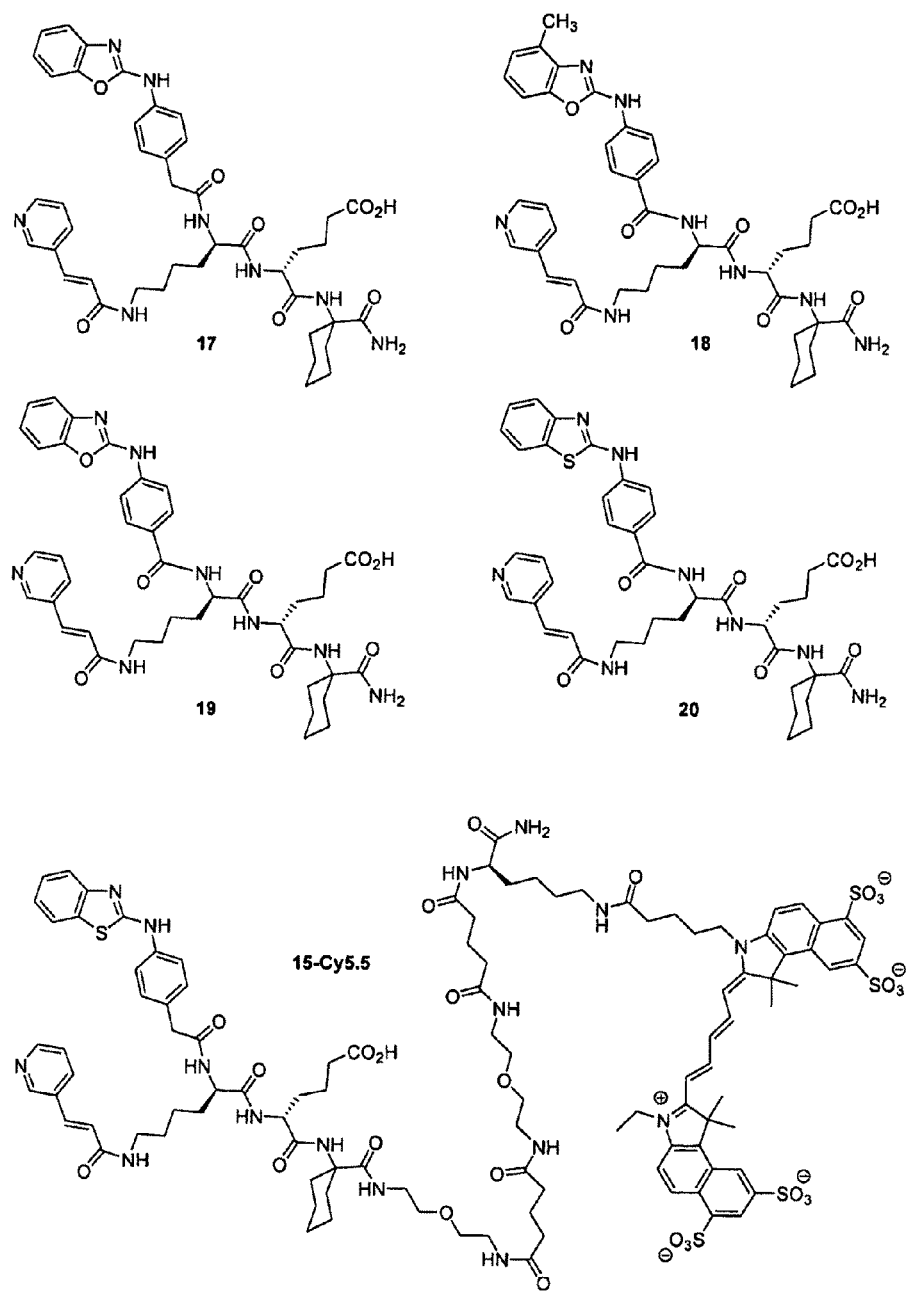
Figure 3:
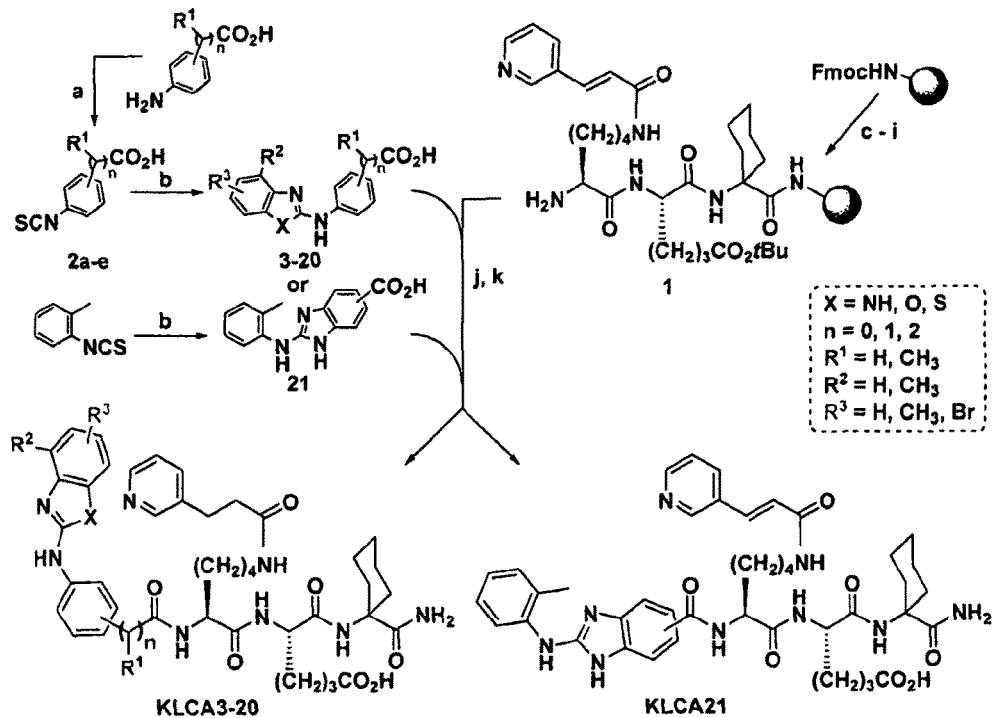
FIG. 3 provides a reaction scheme for the preparation of compounds of the invention.
Figure 4:
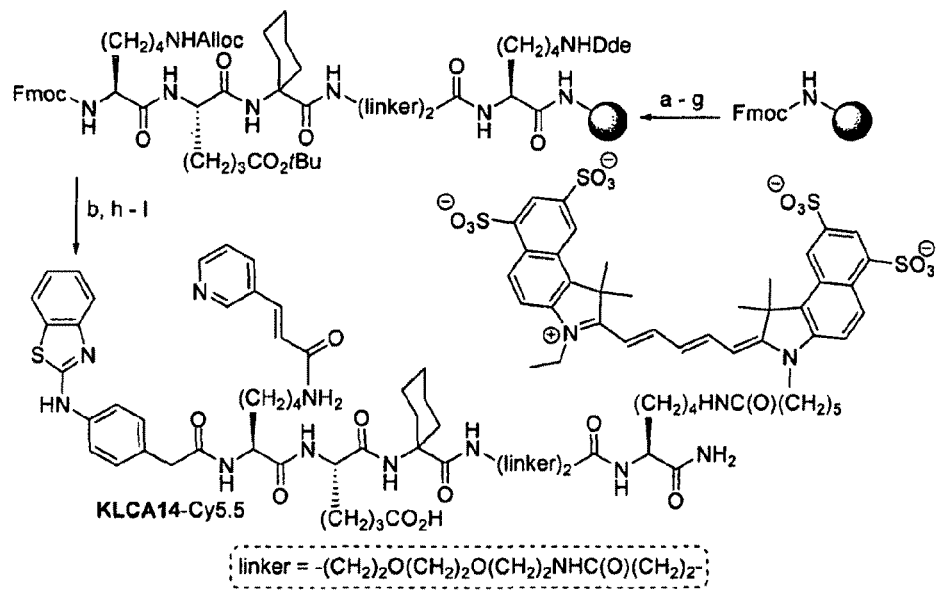
FIG. 4 provides another reaction scheme for the preparation of compounds of the invention.
Figure 5A:
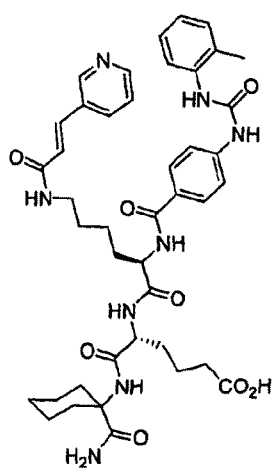
FIG. 5A-5K provides cell adhesion assay graph and $IC_{50}$ values for compounds 2-20.
Figure 5A:
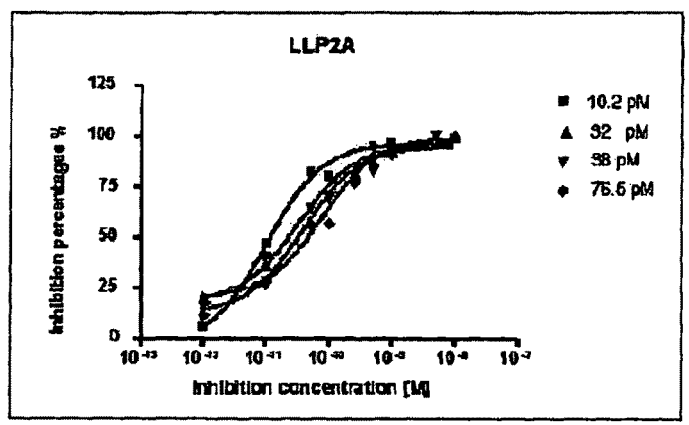
Figure 5A:
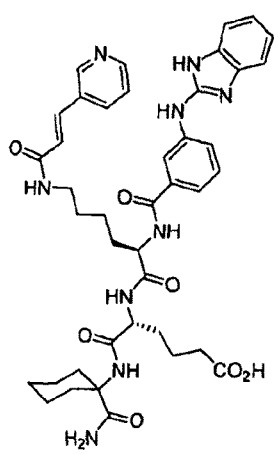
Figure 5A:
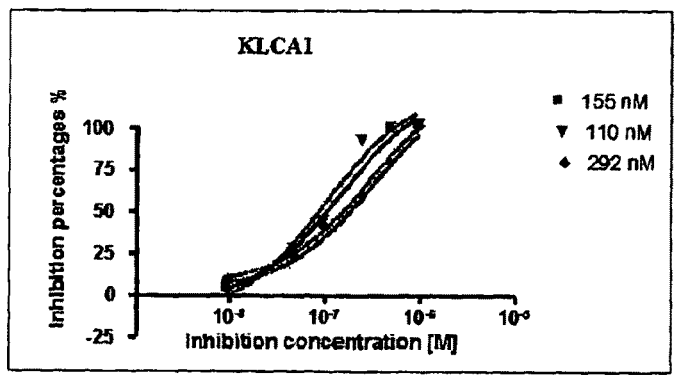
Figure 5B:
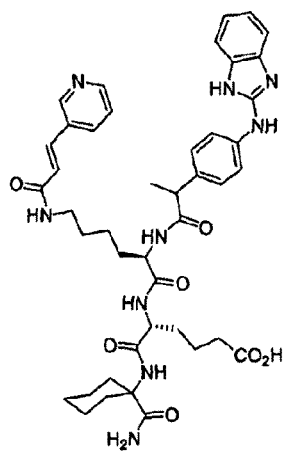
Figure 5B:
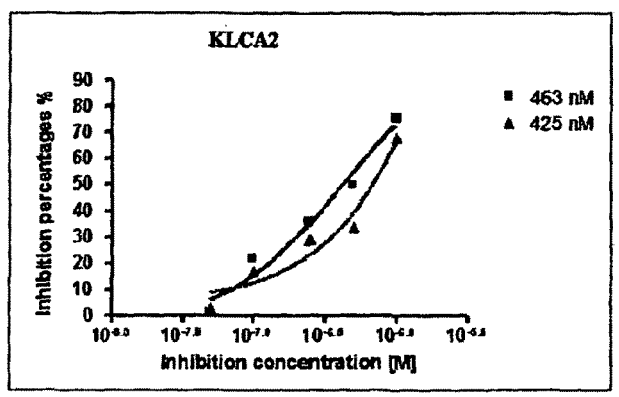
Figure 5B:
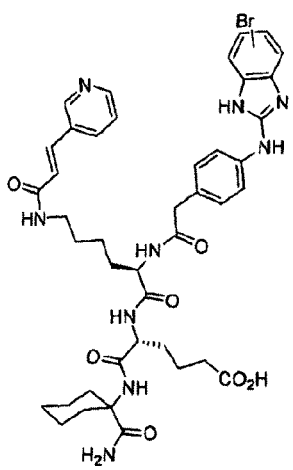
Figure 5B:
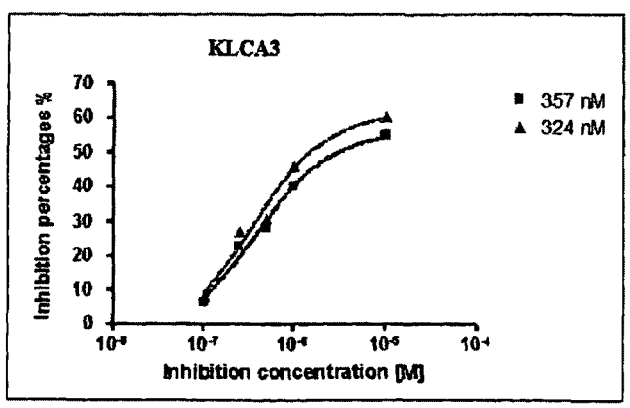
Figure 5C:
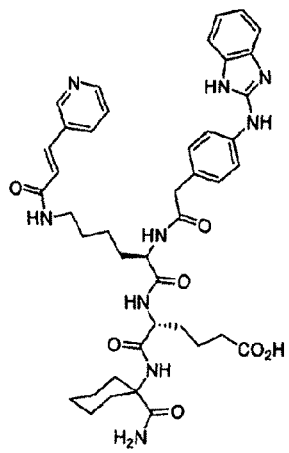
Figure 5C:
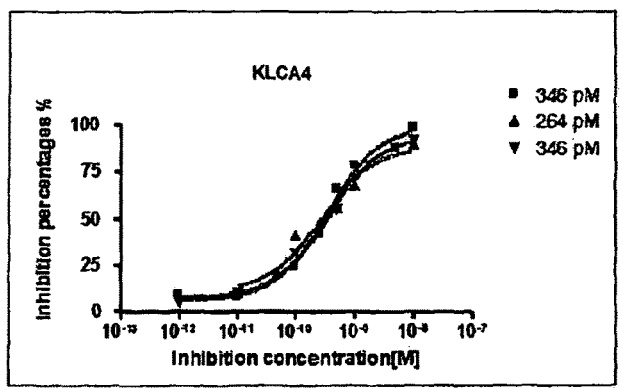
Figure 5C:
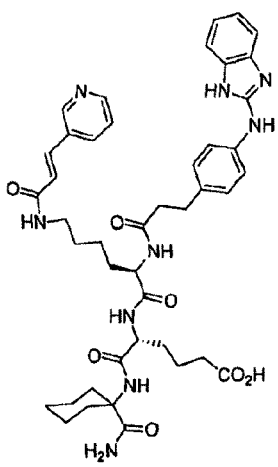
Figure 5C:
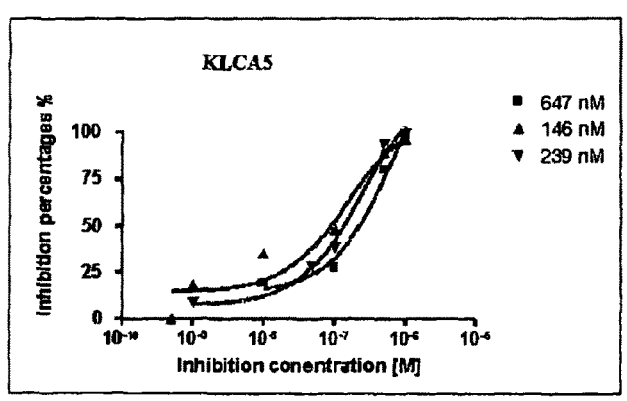
Figure 5D:
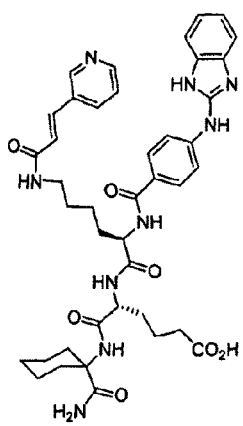
Figure 5D:
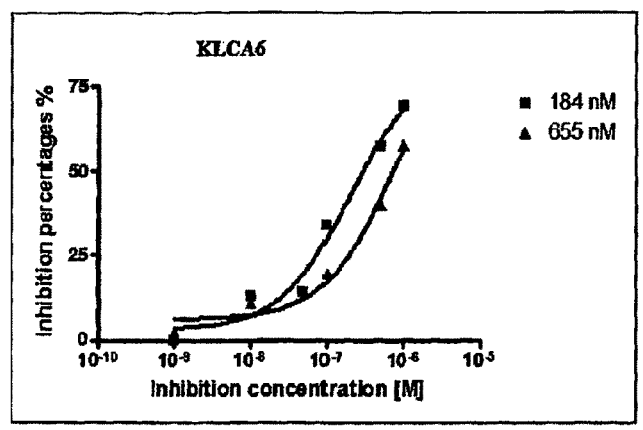
Figure 5D:
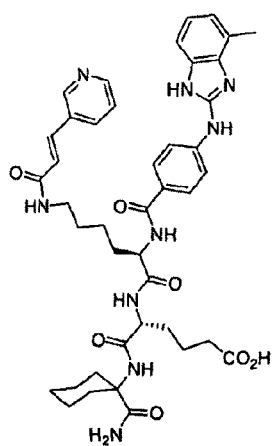
Figure 5D:
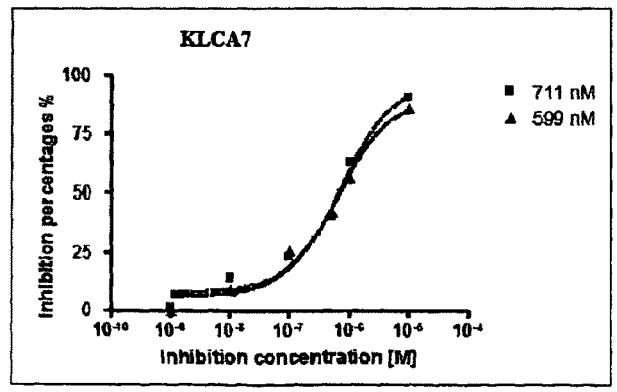
Figure 5E:
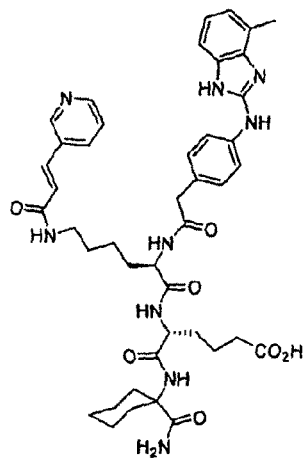
Figure 5E:
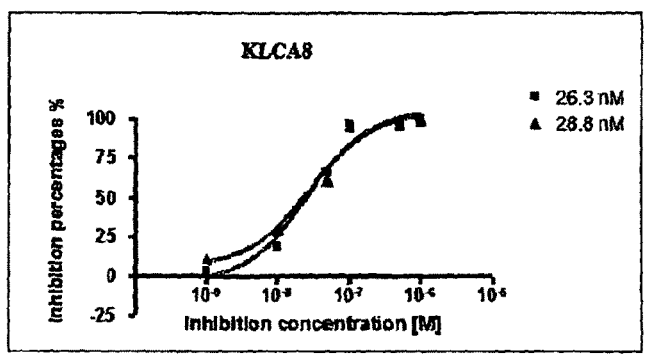
Figure 5E:
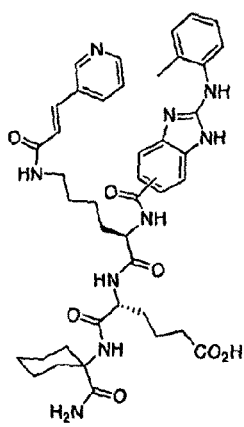
Figure 5E:
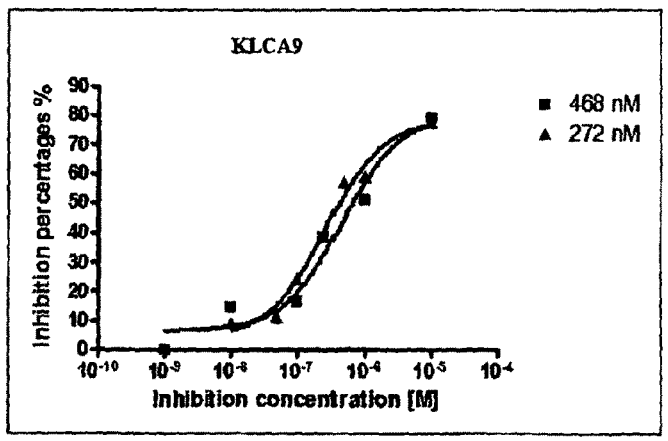
Figure 5F:
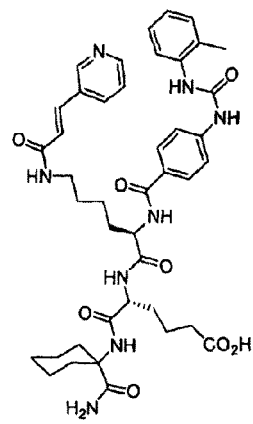
Figure 5F:
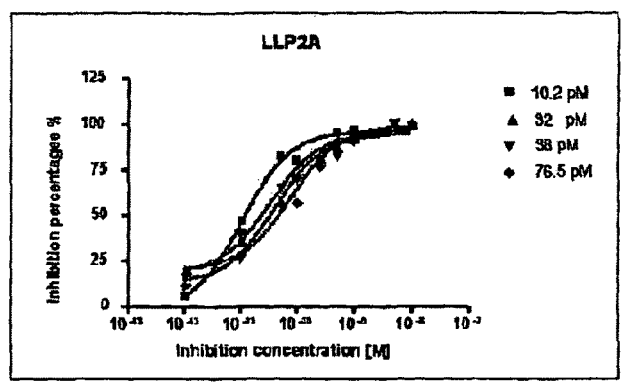
Figure 5F:
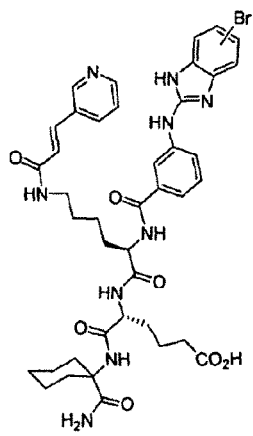
Figure 5F:
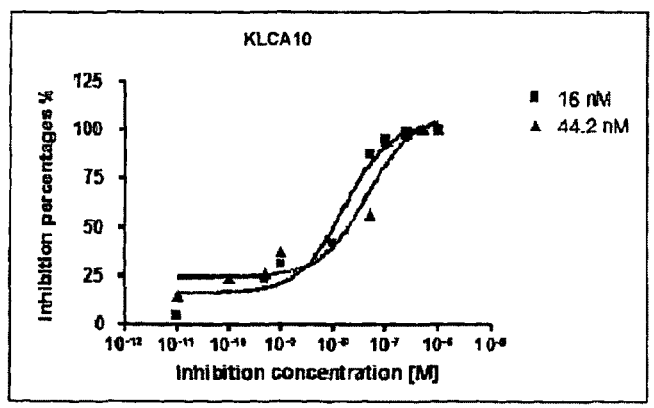
Figure 5G:
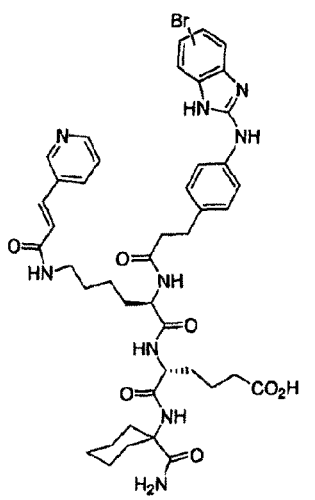
Figure 5G:
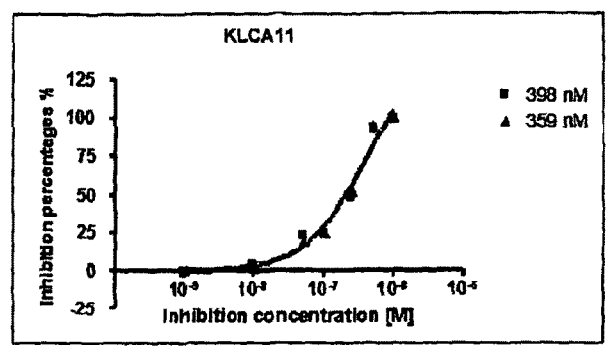
Figure 5G:
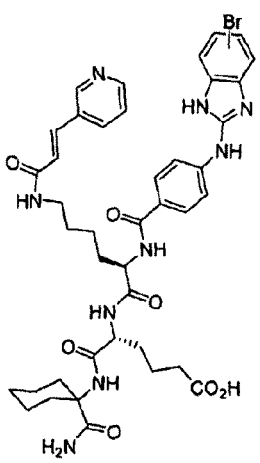
Figure 5G:
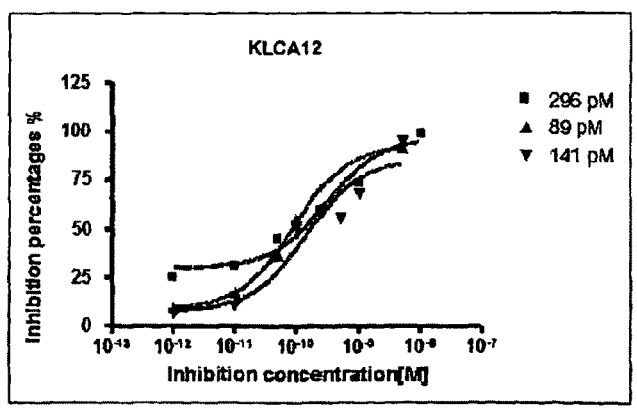
Figure 5H:
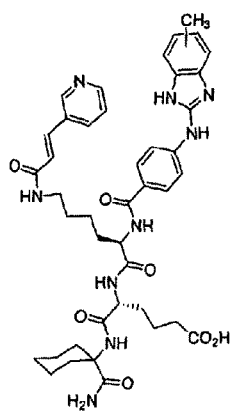
Figure 5H:
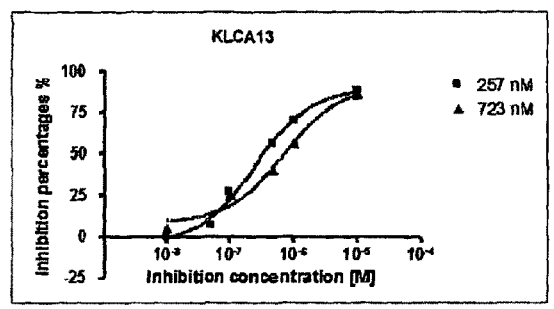
Figure 5H:
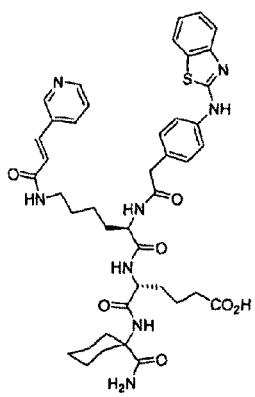
Figure 5H:
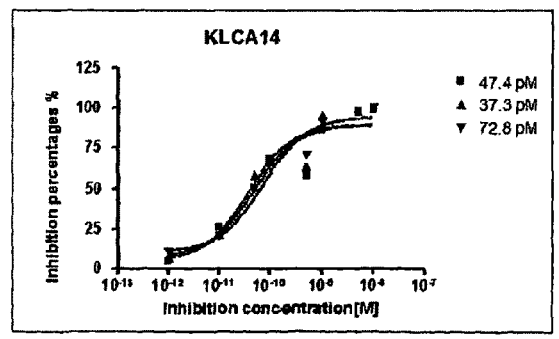
Figure 5I:
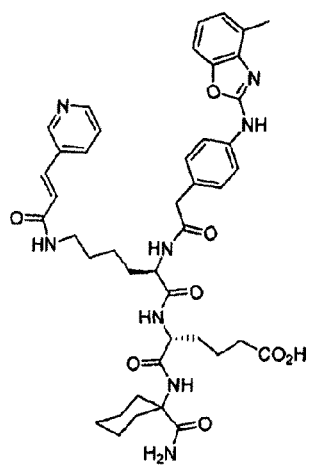
Figure 5I:
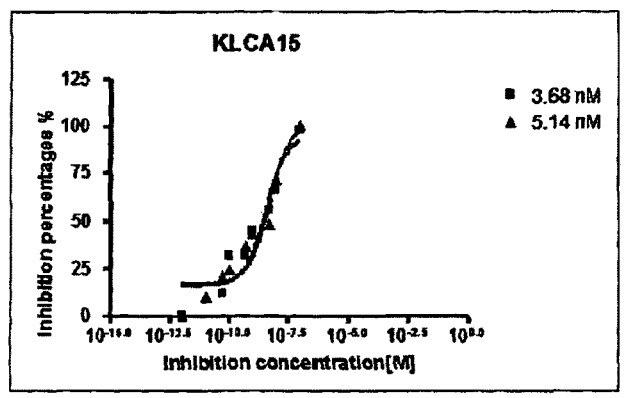
Figure 5I:
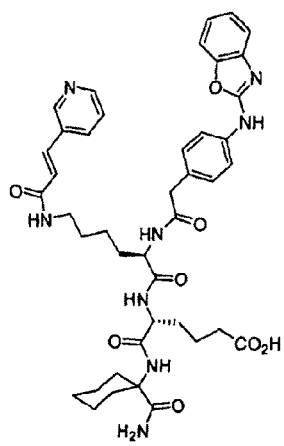
Figure 5I:
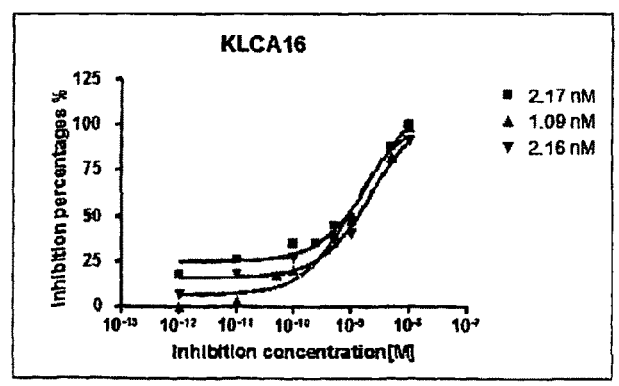
Figure 5J:
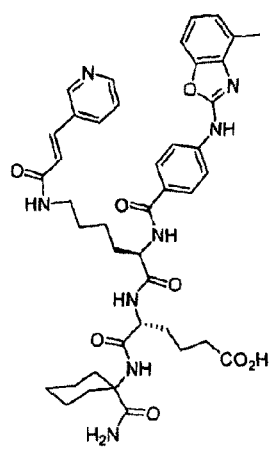
Figure 5J:
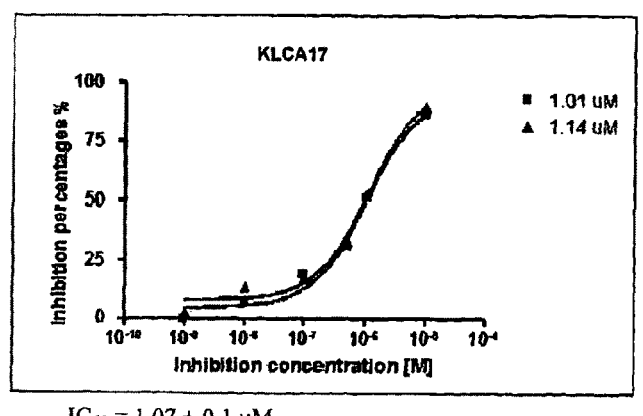
Figure 5J:
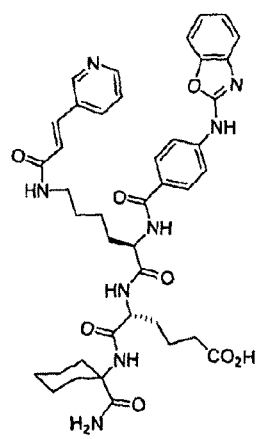
Figure 5J:
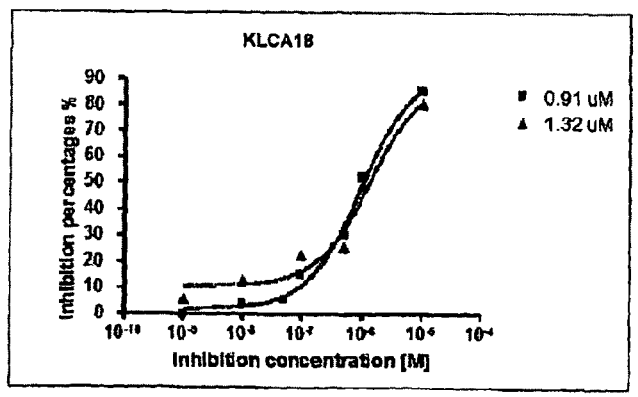
Figure 5K:
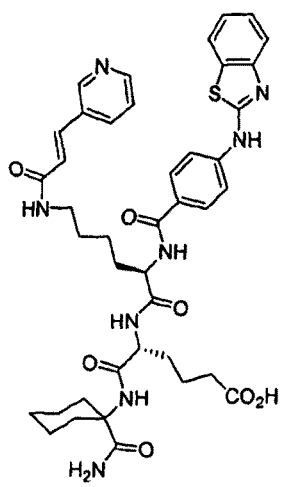
Figure 5K:
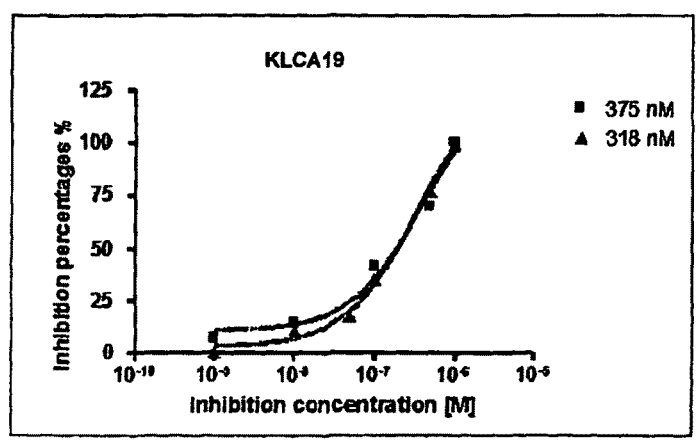

As used herein, the following terms have the meanings ascribed to them unless specified otherwise.

The term "amino acid" refers to naturally-occurring α-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (H is), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups. Suitable unnatural amino acids include, without limitation, 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine (Tyr(3,5-diNO$_2$)), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo[3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S,5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, ornithine (Orn) and α,γ-diaminobutyric acid (Dbu), stereoisomers thereof, and combinations thereof (see, Liu and Lam, *Anal. Biochem.*, 295:9-16 (2001)). As such, the unnatural α-amino acids are present either as unnatural L-α-amino acids, unnatural D-α-amino acids, or combinations thereof.

Suitable phenylalanine analogs include, without limitation, homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-diOMe)), 3,4-difluorophenylalanine (Phe(3,4-diF)), 3,5-difluorophenylalanine (Phe(3,5-diF)), 2,4-dichlorophenylalanine (Phe(2,4-diCl)), 3,4-dichlorophenylalanine (Phe(3,4-diCl)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe(F$_5$)), 3,4,5-trifluorophenylalanine (Phe(F₃)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr(Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), ornithine (Orn) and Dbu, include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Oral, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. See, Table 5 for a description of the structures for each of the lysine derivatives. Derivatives of Orn and Dbu are similar to the lysine derivatives with corresponding carboxylic acid attached to the side chain of Orn and Dbu, respectively.

Suitable N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO₂), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH₂), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF₃), N-methyl-Phe(4-CF₃), N-methyl-Phe(4-NO₂), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys 12, N-methyl-Lys 123, N-methyl-Lys63, N-methyl-Lys 124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

"Amino acid mimetics" are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

"N-substituted glycines" are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Examples of N-substituted glycines suitable for use in the present invention include, without limitation, N-(2-aminoethyl)glycine, N-(3-aminopropyl)glycine, N-(2-methoxyethyl)glycine, N-benzylglycine, (S)—N-(1-phenylethyl)glycine,N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (Miller et al., Drug Dev. Res., 35:20-32 (1995)). As such, peptoids containing at least one unnatural α-amino acid, D-amino acid, or a combination thereof are within the scope of the present invention.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, 1984).

The term "peptide" refers to a compound made up of a single chain of D- or L-amino acids or a mixture of D- and L-amino acids joined by peptide bonds. Generally, peptides are about 2 to about 50 amino acids in length. Preferably, the peptides of the present invention are about 2 to about 25 amino acids in length, more preferably 3 to 20 amino acids in length, and most preferably 3 to 7 amino acids in length.

The term "cancer" refers to any of various malignant neoplasms characterized by the proliferation of anaplastic cells that tend to invade surrounding tissue and metastasize to new body sites. Examples of different types of cancer suitable for treatment using the present invention include, but are not limited to, ovarian cancer, breast cancer, lung cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, osteogenic sarcomas, fibrosarcoma, neuroblastoma, glioma, melanoma, leukemia, and lymphoma.

The term "leukemia" refers to a malignant disease, i.e., cancer, of the bone marrow and blood characterized by the uncontrolled accumulation of blood cells. Leukemia is divided into myelogenous or lymphocytic leukemia, each of which can be acute or chronic. The terms myelogenous or lymphocytic denote the cell type involved. Examples of the types of leukemia suitable for treatment using the present invention include, but are not limited to, acute lymphocytic leukemia, chronic lymphocytic leukemia, acute myelogenous leukemia, chronic myelogenous leukemia, and hairy cell leukemia.

The term "lymphoma" refers to a group of cancers that originates in the lymphatic system. Lymphoma results when a lymphocyte (i.e., a type of white blood cell) undergoes a malignant change and begins to multiply, eventually crowding out healthy cells and creating tumors which enlarge the lymph nodes or other sites in the body. Examples of the types of lymphoma suitable for treatment using the present invention include, but are not limited to, non-Hodgkin's lymphoma, Hodgkin's lymphoma, B-cell lymphoma, acute lymphocytic leukemia, chronic lymphocytic leukemia, T-cell lymphoma, multiple myeloma, hairy cell leukemia, other cancers expressing $\alpha_4\beta_1$-integrin and Burkitt's lymphoma.

The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, inflammatory bowel disease (IBD), rheumatoid diseases such as rheumatoid arthritis, fibrositis, pelvic inflammatory disease, acne, psoriasis, actinomycosis, dysentery, biliary cirrhosis, asthma, Lyme disease, heat rash, Stevens-Johnson syndrome, mumps, pemphigus vulgaris, and blastomycosis.

The term "autoimmune disease" refers to a disease or disorder resulting from an immune response against a self tissue or tissue component and includes a self antibody response or cell-mediated response. The term autoimmune disease, as used herein, encompasses organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis. The term autoimmune disease also encompasses non-organ specific autoimmune diseases, in which an autoimmune response is directed against a component present in several or many organs throughout the body. Such autoimmune diseases include, for example, systemic lupus erythematosus, progressive systemic sclerosis and variants, polymyositis, and dermatomyositis. Additional autoimmune diseases include, but are not limited to, pernicious anemia, primary biliary cirrhosis, autoimmune thrombocytopenia, Sjögren's syndrome, and multiple sclerosis.

The term "therapeutically effective amount" refers to the amount of a compound of the present invention that is capable of achieving a therapeutic effect in a subject in need thereof. For example, a therapeutically effective amount of a compound of the present invention can be the amount that is capable of preventing or relieving one or more symptoms associated with cancer or an inflammatory or autoimmune disease. One skilled in the art will appreciate that the compounds of the present invention can be co-administered with other therapeutic agents (e.g., ions, small organic molecules, peptides, proteins, polypeptides, oligosaccharides, etc.) such as anti-cancer, anti-inflammatory, or immunosuppressive agents.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a compound of the present invention for preventing or relieving one or more symptoms associated with cancer or an inflammatory or autoimmune disease. By "co-administer" it is meant that a compound of the present invention is administered at the same time, just prior to, or just after the administration of a second drug (e.g., anti-cancer agent, anti-inflammatory agent, immunosuppressive agent, etc.).

The term "imaging moiety" refers to a label that is attached to the compounds of the present invention for imaging a tumor, organ, or tissue in a subject. The imaging moiety can be covalently or non-covalently attached to the compound. Examples of imaging moieties suitable for use in the present invention include, without limitation, radionuclides, biotin, fluorophores such as fluorescein, rhodamine, Texas Red, Cy2, Cy3, or Cy5, antibodies, horseradish peroxidase, alkaline phosphatase, derivatives thereof, and mixtures thereof. Exemplary methods for synthesizing the compounds of the present invention as a conjugate are provided below. One skilled in the art will know of other suitable methods for conjugating a particular imaging moiety to the compounds of the present invention.

The term "chelating agent" refers to a compound which binds to a metal ion, such as a radionuclide, with considerable affinity and stability. In addition, the chelating agents of the present invention are bifunctional, having a metal ion chelating group at one end and a reactive functional group capable of binding to peptides, polypeptides, or proteins at the other end. Suitable bifunctional chelating agents include, but are not limited to, 1,4,7,10-tetraazacyclododecane-N,N',N'',N'''-tetraacetic acid (DOTA), a bromoacetamidobenzyl derivative of DOTA (BAD), 1,4,8,11-tetraazacyclotetradecane-N,N',N'',N'''-tetraacetic acid (TETA), diethylenetriaminepentaacetic acid (DTPA), the dicyclic dianhydride of diethylenetriaminepentaacetic acid (ca-DTPA), 2-(p-isothiocyanatobenzyl)-diethylenetriaminepentaacetic acid (SCNBzDTPA), and 2-(p-isothiocyanatobenzyl)-5(6)-methyl-diethylenetriaminepentaacetic acid (MxDTPA) (see, Ruegg et al., *Cancer Research*, Vol. 50: 14 4221-4226, 1990; DeNardo et al., *Clinical Cancer Research*, Vol. 4: 10 2483-2490, 1998). Other chelating agents include EDTA, NTA, HDTA and their phosphonate analogs such as EDTP, HDTP, NTP (see, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989; and references contained therein).

The term "radionuclide" refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 ($^{18}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for meta state. Additionally, naturally occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{82}Rb$, and $^{86}Y$ are examples of positron-emitting radionuclides. $^{64}Cu$ is a beta- and positron-emitting radionuclide.

The term "linker" refers to a moiety that possesses one or more different reactive functional groups that allows for covalent attachment of moieties such as a peptide to a chelating agent. Preferably, the linking moiety possesses two different reactive functional groups, i.e., a heterobifunctional linker. Suitable linkers include, without limitation, those available from Pierce Biotechnology, Inc. (Rockford, Ill.). In preferred embodiments of the present invention, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached. As used herein, the term "chelating agent-linker conjugate" refers to a chelating agent covalently attached to a linker. Such chelating agent-linker conjugates can be attached to a peptide via a functional group present on the linker.

II. General Overview

The present invention provides novel heterocyclic $\alpha_4\beta_1$ integrin ligands (i.e., inhibitors) that advantageously display high binding affinity, specificity, and stability, and methods of their use for imaging a tumor, organ, or tissue in a subject and for treating cancer, inflammatory diseases, and autoimmune diseases.

The present invention is based on the surprising discovery that $\alpha_4\beta_1$ integrin ligands containing a combination of naturally-occurring amino acids, unnatural amino acids, and D-amino acids with a heterocyclic group attached via a peptide bond at the amino-terminus have the following advantageous properties: (1) the ligands bind to $\alpha_4\beta_1$ integrin with high specificity and affinity; (2) the ligands also bind with high specificity and affinity to tumor cells (e.g., leukemia cells); (3) the ligands are resistant to cleavage and/or degradation from proteases found, for example, in plasma, the gastrointestinal tract, and tumor cells; and (4) the ligands have an increased aqueous solubility relative to BIO-1211 and some ligands described in U.S. Ser. No. 11/140,548 filed May 26, 2005. These unique features make the ligands of the present invention particularly useful as imaging agents for localizing tumors and as therapeutic agents for the treatment of cancer (e.g., lymphocytic leukemia, lymphoma and multiple myeloma) as well as other diseases and disorders such as inflammatory diseases, autoimmune diseases, etc.

The compounds provided in the present invention derive from the transformation of the pharmacophore of 1 from a bisaryl urea to a conformationally constrained 2-arylaminobenzimidazole, -benzoxazole, or -benzothiazole system. These systems were designed to exploit one or more of the benzimidazole-mediated physicochemical properties (or related properties for the benzoxazole or benzothiazole compounds)—in particular its extensive pi-orbital system, combination of hydrogen bond acceptors/donors, polarity, and relative acidity of the 2-arylaminobenzimidazole N—H proton (pKa=6.4-7.0). The latter factors, alone or in combination typically improve aqueous solubility. Moreover, the benzimidazole ring system, having rich and diverse pharmaceutical applications that address a variety of ailments, is an important member of the class of heterocycles having heteroatoms at the 1- and 3-positions with this class comprising nearly one quarter of the top 100 selling drugs. As a consequence, N-aryl-2-aminobenzimidazoles facilitate favorable pharmacodynamics and pharmacokinetics (PK), thereby making them ideal components of drug compounds.

III. Description of the Embodiments

In one aspect, the present invention provides compounds having formula I(a) or I(b):

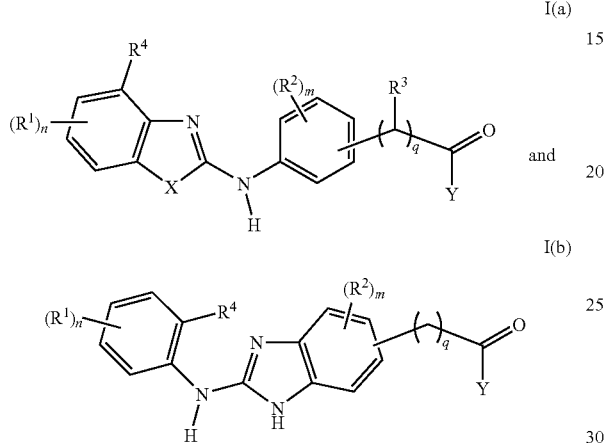

wherein
the subscripts n, m and q are each independently selected integers of from 0 to 2;
$R^1$ is selected from the group consisting of hydrogen, halogen, $C_1$-$C_4$ alkyl, $C_1$-$C_4$ alkoxy, and $C_1$-$C_4$ haloalkyl;
$R^2$ is selected from the group consisting of hydrogen, halogen, $C_1$-$C_4$ alkyl and $C_1$-$C_4$ alkoxy;
$R^3$ is selected from the group consisting of hydrogen, $C_1$-$C_4$ alkyl and $C_3$-$C_8$ cycloalkyl;
$R^4$ is H or $CH_3$;
X is S, O or NH;
Y is a peptide having r independently selected amino acids, wherein at least one amino acid is selected from the group consisting of an unnatural amino acid and a D-amino acid; and
r is an integer of from 3 to 20.

In a first embodiment, $R^4$ is —$CH_3$. In a second embodiment, $R^3$ is —H. In a third embodiment, the halogen (of $R^1$ and $R^2$) is independently selected from the group consisting of —F, —Cl, —Br, and —I. In a fourth embodiment, the $C_3$-$C_8$ cycloalkyl group is selected from the group consisting of a cyclopropyl group, a cyclopentyl group, and a cyclohexyl group. In a fifth embodiment, the $C_1$-$C_4$ haloalkyl group is —$CF_3$. In a sixth embodiment, the $C_1$-$C_4$ alkoxy group is a methoxy group.

Certain heterocyclic components of I(a) and I(b) include: when q is 0:

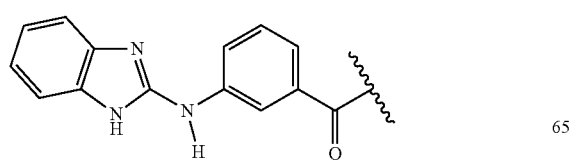

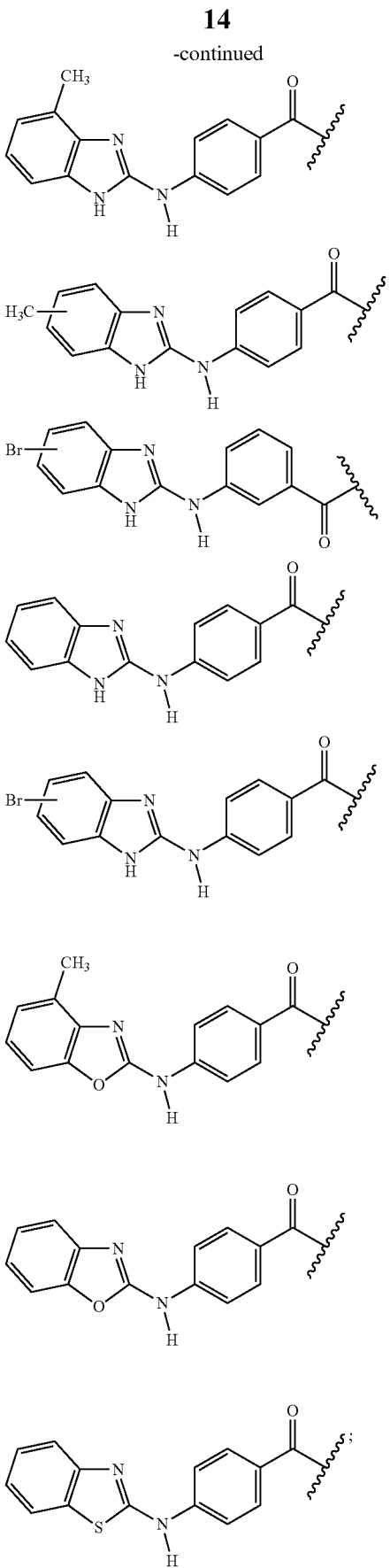

when q is 1:

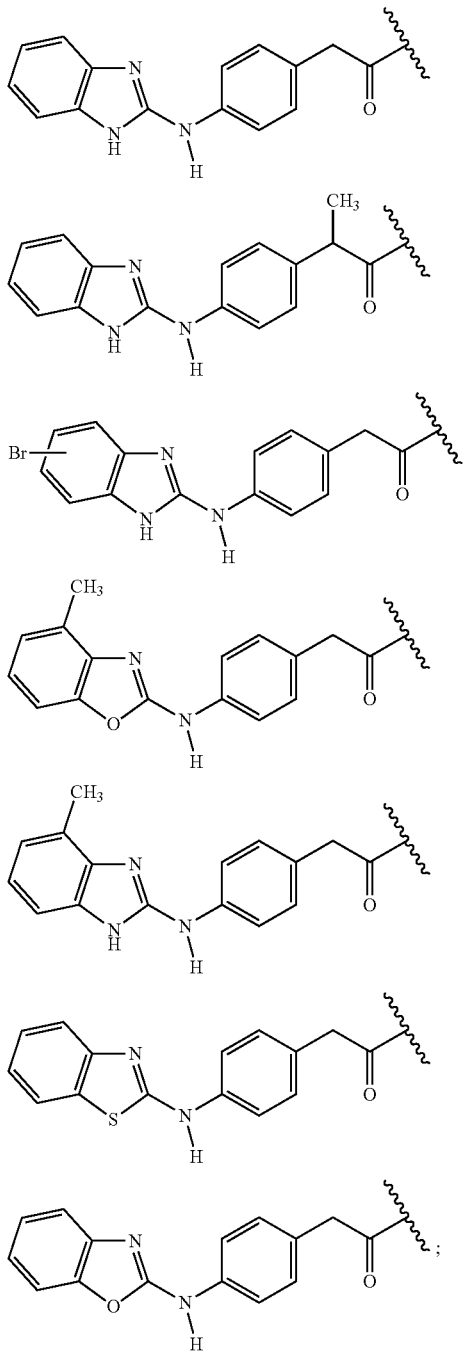

and, when q is 2:

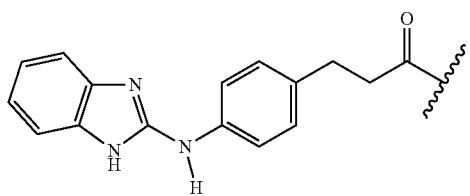

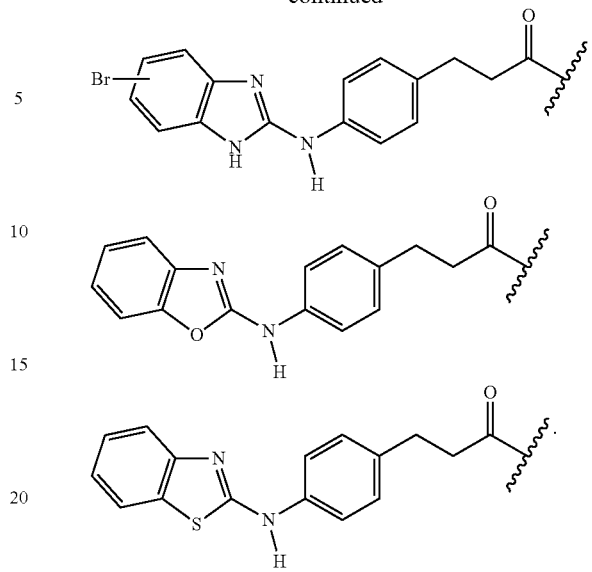

Turning next to the Y component of formula I(a) and I(b), the amino acids are selected from the group consisting of naturally-occurring amino acids; unnatural amino acids such as amino acid analogs, amino acid mimetics, synthetic amino acids, N-substituted glycines, N-methyl amino acids; stereoisomers thereof; and combinations thereof.

In one embodiment; the unnatural amino acid is selected from the group consisting of 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine (Tyr(3,5-diNO$_2$)), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), homolysine (Hly), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo[3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid, (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S,5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, homolysine (Hly), ornithine (Orn) and α,γ-diaminobutyric acid (Dbu), stereoisomers thereof, and combinations thereof.

Suitable phenylalanine analogs include, without limitation, homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-diOMe)), 3,4-difluorophenylalanine (Phe(3,4-diF)), 3,5-difluorophenylalanine (Phe(3,5-diF)), 2,4-dichlorophenylalanine (Phe(2,4-diCl)), 3,4-dichlorophenylalanine (Phe(3,4-diCl)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe(F$_5$)), 3,4,5-trifluorophenylalanine (Phe(F$_3$)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr(Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), Hly, Orn and Dbu include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Hly38, Hly27, Hly73, Hly55, Hly28, Hly72, Hly12, Hly123, Hly63, Hly124, Hly82, Hly31, Hly15, Hly125, Hly43, Hly24, Hly5, Hly4, Hly50, Hly81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof.

Suitable N-methyl amino acids include, N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO$_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH$_2$), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF$_3$), N-methyl-Phe(4-CF$_3$), N-methyl-Phe(4-NO$_2$), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys 12, N-methyl-Lys 123, N-methyl-Lys63, N-methyl-Lys 124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Hly38, N-methyl-Hly27, N-methyl-Hly73, N-methyl-Hly55, N-methyl-Hly28, N-methyl-Hly72, N-methyl-Hly12, N-methyl-Hly123, N-methyl-Hly63, N-methyl-Hly124, N-methyl-Hly82, N-methyl-Hly31, N-methyl-Hly15, N-methyl-Hly125, N-methyl-Hly43, N-methyl-Hly24, N-methyl-Hly5, N-methyl-Hly4, N-methyl-Hly50, N-methyl-Hly81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

In another embodiment, the D-amino acid is selected from the group consisting of a D-α-amino acid, a D-β-amino acid, a D-γ-amino acid, and a combination thereof. In yet another embodiment, the D-α-amino acid is selected from the group consisting of a stereoisomer of a naturally-occurring α-amino acid, an unnatural D-α-amino acid, and a combination thereof. In still yet another embodiment, the stereoisomer of a naturally-occurring α-amino acid is selected from the group consisting of D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. In a further embodiment, n is an integer of from 3 to 15, preferably of from 3 to 10, and more preferably of from 3 to 7.

In certain instances, Y is a tetrapeptide having the following structure:

$$-Y^1-Y^2-Y^3-Y^4,$$

wherein $Y^1$ is selected from the group consisting of a hydrophobic amino acid and derivatives of lysine, homolysine (Hly), ornithine (Orn) and α,γ-diaminobutyric acid (Dbu); $Y^2$ is a negatively charged amino acid; $Y^3$ is a hydrophobic amino acid; and $Y^4$ is selected from the group consisting of a naturally-occurring amino acid, an unnatural amino acid, and a D-amino acid. In one group of embodiments, $Y^4$ has a carboxyl-terminal group selected from an amide group and a carboxylic acid group.

Preferably, the hydrophobic amino acids are independently selected from the group consisting of leucine (Leu), a leucine analog, phenylalanine (Phe), a phenylalanine analog, proline (Pro), a proline analog, valine (Val), isoleucine (Ile), glycine (Gly), alanine (Ala), norvaline (Nva), 1-aminocyclopropane-1-carboxylic acid (Acpc), 1-aminocyclobutane-1-carboxylic acid (Acb), α-cyclohexylglycine (Chg), α-aminoisobutyric acid (Aib), α-aminobutyric acid (Abu), 3-(2-thienylalanine (2-Thi), 3-(3-thienyl)alanine (3-Thi), 3-(3-pyridyl)alanine (3-Pal), 3-(2-naphthyl)alanine (Nal-2), 2-amino-2-naphthylacetic acid (Ma), 3,5-dinitrotyrosine (Tyr(3,5-diNO$_2$)), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 2-aminoindane-2-carboxylic acid (Aic), (2S,5R)-5-phenylpyrrolidine-2-carboxylic acid (Ppca), 4-thiazoylalanine (Tha), 2-aminooctanoic acid (Aoa), 2-aminoheptanoic acid (Aha), and stereoisomers thereof.

Suitable leucine analogs include, without limitation, norleucine (Nle), homoleucine (Hle), propargylglycine (Pra), cyclopropylalanine (Cpa), cylobutylalanine (Cba), cyclopentylalanine, cyclohexylalanine (Cha), and stereoisomers thereof.

Additionally, the proline analog is selected from the group consisting of hydroxyproline (Hyp), O-benzyl-hydroxyproline (Hyp(Bzl)), homoproline (HoPro), β-homoproline (βHoPro), thiazolidine-4-carboxylic acid (Thz), 1-aminocyclopentane-1-carboxylic acid (Acp), (2S,5R)-5-phenylpyrrolidine-2-carboxylic acid (Ppca), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 3-aminobenzoic acid (3-Abz), and 5H-thiazolo[3,2-a]pyridine-3-carboxylic acid (Btd), and stereoisomers thereof.

In some embodiments, the derivatives of lysine (Lys), Orn and Dbu are selected from the group consisting of Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Hly38, Hly27, Hly73, Hly55, Hly28, Hly72, Hly12, Hly123, Hly63, Hly124, Hly82, Hly31, Hly15, Hly125, Hly43, Hly24, Hly5, Hly4, Hly50, Hly81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof.

In some embodiments, the negatively charged amino acid is selected from the group consisting of aspartic acid (Asp), glutamic acid (Glu), α-aminohexanedioic acid (Aad), α-aminooctanedioc acid (Asu), homoaspartic acid (HoAsp), γ-carboxy-glutamic acid, 4-carboxyphenylalanine (Phe(4-COOH)), and stereoisomers thereof.

More particularly, $Y^1$ is selected from the group consisting of Leu, a leucine analog, Lys38, and stereoisomers thereof. More particularly, $Y^2$ is selected from the group consisting of Asp, Glu, Aad, and stereoisomers thereof. In some preferred embodiments, $Y^2$ is Aad. In still other embodiments, $Y^3$ is selected from the group consisting of Leu, a leucine analog, Phe, a phenylalanine analog, Val, Ile, Ala, Nva, Acpc, Chg, Aib, Abu, Aic, Nal-2, Ana, and stereoisomers thereof. In yet other embodiments, $Y^4$ is selected from the group consisting of a hydrophobic amino acid, a negatively charged amino acid, and stereoisomers thereof. Preferably, the hydrophobic amino acid is selected from the group consisting of Pro, a proline analog, and stereoisomers thereof. Still more preferably, the proline analog is Hyp.

In a particularly preferred group of embodiments, Y is selected from the group consisting of -Nle-Aad-Chg-D-Tyr, -Leu-Aad-Val-Hyp, -Hle-Aad-Phe-Chg, -Lys38-Aad-Leu-D-Pro, -Cpa-Aad-Ile-D-Asp, -Hle-Aad-Aib-D-3-Pal, -Leu-Aad-Ala-Hyp, -Cpa-Asp-Nva-D-Glu, -Cpa-Aad-Aib-D-Thi, -Cpa-Aad-Acpc-Hyp, -Nle-Aad-Val-D-Glu, -Lys38-Aad-Acpc-D-Asp, -Lys38-Aad-D-Phe-D-3-Pal, -Cpa-Aad-Nle-D-Pro, -Lys-Aad-Chg-D-Glu, -Cpa-Aad-Nle-Aad, -Cpa-Aad-Acpc-Aad, -Leu-Aad-Acpc-Aad, -HoPhe-Aad-D-Nal-2-D-Glu, -Lys38-Aad-D-Phe-D-Asp and -Lys38-Aad-D-Phe-D-Val.

Still more preferably, Y is selected from the group consisting of -Nle-Glu-Ala-D-Thi, -Cha-Asp-Nle-D-Gln, -Leu-Asp-D-Phe-Aic, -Cpa-Asp-Leu-D-Thi, -HoPhe-Asp-Abu-D-Asn, -Hle-Asp-Acpc-D-Ala, -Leu-Aad-Ana-D-Pro, -Lys38-Asp-Phe(3-Cl)-D-Pro, -Cpa-Asp-Ala-D-Thi, and -HoPhe-Asp-Ala-Hyp.

In certain other instances, Y is a tripeptide having the following structure:

$$-Y^1-Y^2-Y^3,$$

wherein $Y^1$ is selected from the group consisting of a hydrophobic amino acid and derivatives of lysine, homolysine (Hly), ornithine (Orn) and α,γ-diaminobutyric acid (Dbu); $Y^2$ is a negatively charged amino acid; and $Y^3$ is a hydrophobic amino acid.

The hydrophobic amino acid includes any of the hydrophobic amino acids described above. Likewise, the lysine derivative includes any of the lysine derivatives described above. Preferably, $Y^1$ is Lys-38. The negatively charged amino acid includes any of the negatively charged amino acids described above. Preferably, $Y^2$ is α-aminohexanedioic acid (Aad). In certain instances, $Y^3$ is a D-amino acid. In a preferred embodiment, Y is selected from the group consisting of -Lys38-Aad-D-Phe, -Lys38-Aad-Ach, -Lys38-Aad-D-Nal-2, -Lys38-Aad-Ile, -Lys38-Aad-Val, and -Lys38-Aad-Leu. More preferably, Y is -Lys38-Aad-Ach. Still more preferably, the compounds of this group bind to cells selected from the group consisting of malignant T-cells, malignant B-cells, cancer cells with α1,β2 integrins and multiple myeloma cells. In another group of embodiments, Y is -Nle-Aad-Phg. In yet another embodiment, the compound does not bind to non-leukemia cells.

In a particularly preferred embodiment, the compound is one of compounds 2-20 in FIGS. 2A, 2B, 2C and 2D.

In a related aspect, the present invention provides multimers or oligomers of the compounds provided herein. In particular, multimers or oligomers are provided in which a plurality of the compounds (e.g., the ligands) are attached to a scaffolding such as a polyethylene glycol scaffolding to provide higher molecular weight conjugates. One of skill in the art will appreciate that a number of scaffolds are commercially available and can be used to confer various properties such as water solubility, and provide, in some embodiments, varying degrees of compound removal from the scaffold. In the latter instance, different linkages to the scaffold can alter the rates by which hydrolytic enzymes release the compound or degrade the scaffold.

In another aspect, the present invention provides a method for treating cancer in a subject in need thereof, the method comprising:

administering to the subject an effective amount of a compound having the formula:

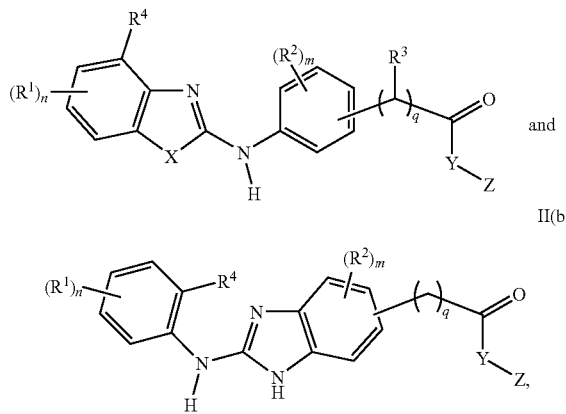

II(a)

II(b)

wherein
the subscripts n, m and q are each independently selected integers of from 0 to 2;
$R^1$ is selected from the group consisting of hydrogen, halogen, $C_1$-$C_4$ alkyl, $C_1$-$C_4$ alkoxy, and $C_1$-$C_4$ haloalkyl;
$R^2$ is selected from the group consisting of hydrogen, halogen, $C_1$-$C_4$ alkyl and $C_1$-$C_4$ alkoxy;
$R^3$ is selected from the group consisting of hydrogen, $C_1$-$C_4$ alkyl and $C_3$-$C_8$ cycloalkyl;
$R^4$ is H or $CH_3$;
X is S, O or NH;
Y is a peptide having r independently selected amino acids, wherein at least one amino acid is selected from the group consisting of an unnatural amino acid and a D-amino acid;
Z is a chelating agent or a chelating agent-linker conjugate; and
r is an integer of from 3 to 20; wherein the effective amount is an amount sufficient for therapeutic benefit or an amount sufficient to target delivery of an anticancer agent selected from radionuclides, chemotherapeutic agents, nanoparticles, nanodroplets and cytokines.

In one embodiment, the cancer is a lymphoma or leukemia. In another embodiment, the lymphoma or leukemia is selected from the group consisting of non-Hodgkin's lymphoma, Hodgkin's lymphoma, B-cell lymphoma, T-cell lymphoma, multiple myeloma, Burkitt's lymphoma, acute lymphocytic leukemia, chronic lymphocytic leukemia, and hairy cell leukemia, or any other cancers expressing α4β1-integrin. In certain instances, the compound is radiolabeled with a radionuclide by directly attaching the radionuclide to the ligand. In certain other instances, the radionuclide is bound to the chelating agent or chelating agent-linker conjugate attached to the ligand. Suitable radionuclides for direct conjugation include, without limitation, $^{18}$F, $^{124}$I, $^{125}$I, $^{131}$I, and mixtures thereof. Suitable radionuclides for use with a ligand-chelating agent conjugate include, without limitation, $^{47}$SC, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, $^{212}$Bi, and mixtures thereof. Preferably, the radionuclide bound to a chelating agent is $^{64}$Cu, $^{90}$Y, $^{111}$In, or mixtures thereof. Suitable chelating agents include, but are not limited to, DOTA, BAD, TETA, DTPA, EDTA, NTA, HDTA, their phosphonate analogs, and mixtures thereof. One of ordinary skill is familiar with methods for attaching radionuclides, chelating agents, and chelating agent-linker conjugates to the ligands of the present invention. In particular, attachment of radionuclides, chelating agents, and chelating agent-linker conjugates to the ligands of the present invention can be conveniently accomplished using, for example, commercially available bifunctional linking groups (generally heterobifunctional linking groups) that can be attached to a functional group present in a non-interfering position on the compound and then further linked to, for example, a radionuclide, chemotherapeutic agent, anticancer agent, nanoparticle, quantum dot, nanodroplet of an anticancer agent or a small molecule toxin. In this manner, the compounds of the present invention can be used to carry suitable agents to a target site, generally, a tumor or organ or tissue having cancerous cells expressing α4,β1-integrin.

One skilled in the art will also appreciate that the compounds of the present invention can be co-administered with other therapeutic agents for the treatment of cancer. Suitable anti-cancer agents for combination therapy include, without limitation, cytotoxins and agents such as antimetabolites, alkylating agents, anthracyclines, antibiotics, antimitotic agents, procarbazine, hydroxyurea, asparaginase, corticosteroids, interferons, radiopharmaceuticals, peptides with anti-tumor activity such as TNF-α, pharmaceutically acceptable salts thereof; derivatives thereof, prodrugs thereof, and combinations thereof.

In yet another aspect, the present invention provides a method for imaging a tumor, organ, or tissue, the method comprising:
(a) administering to a subject in need of such imaging, a compound having formula II(a) or II(b):

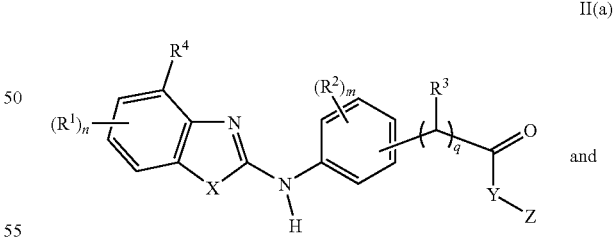

II(a)

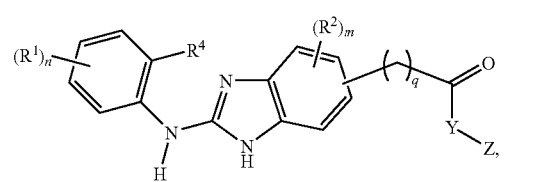

II(b)

wherein
  the subscripts n, m and q are each independently selected integers of from 0 to 2;
  $R^1$ is selected from the group consisting of hydrogen, halogen, $C_1$-$C_4$ alkyl, $C_1$-$C_4$ alkoxy, and $C_1$-$C_4$ haloalkyl;
  $R^2$ is selected from the group consisting of hydrogen, halogen, $C_1$-$C_4$ alkyl and $C_1$-$C_4$ alkoxy;
  $R^3$ is selected from the group consisting of hydrogen, $C_1$-$C_4$ alkyl and $C_3$-$C_8$ cycloalkyl;
  $R^4$ is H or $CH_3$;
  X is S, O or NH;
  Y is a peptide having r independently selected amino acids, wherein at least one amino acid is selected from the group consisting of an unnatural amino acid and a D-amino acid;
  Z is a chelating agent or a chelating agent-linker conjugate; and
  r is an integer of from 3 to 20; and
  (b) detecting the compound to determine where the compound is concentrated in the subject.

In one embodiment, the imaging moiety is selected from the group consisting of a radionuclide, biotin, a fluorophore such as fluorescein, rhodamine, Texas Red, Cy2, Cy3, or Cy5, an antibody, horseradish peroxidase, and alkaline phosphatase. In certain instances, the compound is radiolabeled with a radionuclide by directly attaching the radionuclide to the ligand. In certain other instances, the radionuclide can be bound to a chelating agent attached to the ligand. Suitable radionuclides for direct conjugation include, without limitation, $^{18}F$, $^{131}I$, and mixtures thereof. Suitable radionuclides for use with a ligand-chelating agent conjugate include, without limitation, $^{55}Co$, $^{60}Cu$, $^{61}Cu$, $^{62}Cu$, $^{64}Cu$, $^{66}Ga$, $^{67}Cu$, $^{67}Ga$, $^{68}Ga$, $^{82}Rb$, $^{86}Y$, $^{87}Y$, $^{90}Y$, $^{111}In$, $^{99m}Tc$, $^{201}Tl$, and mixtures thereof. Preferably, the radionuclide bound to a chelating agent is $^{64}Cu$, $^{90}Y$, $^{111}In$, or mixtures thereof. Suitable chelating agents include, but are not limited to, DOTA, BAD, TETA, DTPA, EDTA, NTA, HDTA, their phosphonate analogs, and mixtures thereof. One of ordinary skill in the art will know of methods for attaching radionuclides, chelating agents, and other imaging moieties to the ligands of the present invention.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled compound of the present invention. Positron emission tomography (PET) is another suitable technique for detecting radiation in a subject. Furthermore, U.S. Pat. No. 5,429,133 describes a laparoscopic probe for detecting radiation concentrated in solid tissue tumors. Miniature and flexible radiation detectors intended for medical use are produced by Intra-Medical LLC, Santa Monica, Calif. Magnetic Resonance Imaging (MRI) or any other imaging technique known to one of skill in the art is also suitable for detecting the radioactive emissions of radionuclides. Regardless of the method or device used, such detection is aimed at determining where the compound is concentrated in a subject, with such concentration being an indicator of the location of a tumor or tumor cells.

In still yet another aspect, the present invention provides a method for treating an inflammatory or autoimmune disease in a subject in need thereof, the method comprising:
  administering to said subject a therapeutically effective amount of a compound having the formula:

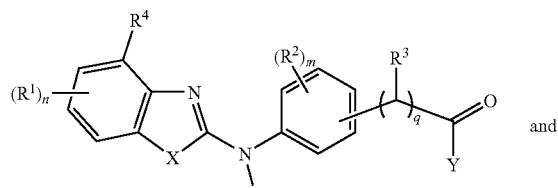

I(a)

and

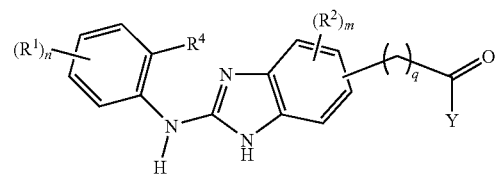

I(b)

wherein
  the subscripts n, m and q are each independently selected integers of from 0 to 2;
  $R^1$ is selected from the group consisting of hydrogen, halogen, $C_1$-$C_4$ alkyl, $C_1$-$C_4$ alkoxy, and $C_1$-$C_4$ haloalkyl;
  $R^2$ is selected from the group consisting of hydrogen, halogen, $C_1$-$C_4$ alkyl and $C_1$-$C_4$ alkoxy;
  $R^3$ is selected from the group consisting of hydrogen, $C_1$-$C_4$ alkyl and $C_3$-$C_8$ cycloalkyl;
  $R^4$ is H or $CH_3$;
  X is S, O or NH;
  Y is a peptide having r independently selected amino acids, wherein at least one amino acid is selected from the group consisting of an unnatural amino acid and a D-amino acid; and
  r is an integer of from 3 to 20.

Any of a variety of inflammatory or autoimmune diseases such as those described above are suitable for treatment with the compounds of the present invention. Preferably, the autoimmune disease is multiple sclerosis, rheumatoid arthritis, or lupus.

One skilled in the art will appreciate that the compounds of the present invention can be co-administered with other therapeutic agents for the treatment of inflammatory or autoimmune diseases. Suitable anti-inflammatory agents for combination therapy include, without limitation, corticosteroids, non-steroidal anti-inflammatory agents, antibodies such as infliximab, 5-aminosalicylates, antibiotics, pharmaceutically acceptable salts thereof; derivatives thereof, prodrugs thereof, and combinations thereof. Suitable immunosuppressive agents for combination therapy include, without limitation, azathioprine and metabolites thereof, anti-metabolites such as methotrexate, immunosuppressive antibodies, mizoribine monophosphate, cyclosporine, scoparone, FK-506 (tacrolimus), FK-778, rapamycin (sirolimus), glatiramer acetate, mycopehnolate, pharmaceutically acceptable salts thereof, derivatives thereof, prodrugs thereof, and combinations thereof.

In certain instances, the compounds of the present invention further comprise a radionuclide, a chelating agent, biotin, a fluorophore, an antibody, horseradish peroxidase, or alkaline phosphatase attached thereto. Such conjugates can be particularly useful, e.g., for therapeutic and/or imaging purposes. Accordingly, in still another aspect, the present invention provides a targeting conjugate having the formula selected from:

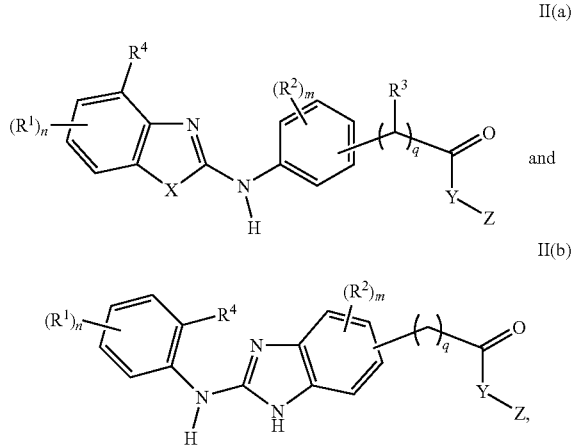

wherein
the subscripts n, m and q are each independently selected integers of from 0 to 2;
$R^1$ is selected from the group consisting of hydrogen, halogen, $C_1$-$C_4$ alkyl, $C_1$-$C_4$ alkoxy, and $C_1$-$C_4$ haloalkyl;
$R^2$ is selected from the group consisting of hydrogen, halogen, $C_1$-$C_4$ alkyl and $C_1$-$C_4$ alkoxy;
$R^3$ is selected from the group consisting of hydrogen, $C_1$-$C_4$ alkyl and $C_3$-$C_8$ cycloalkyl;
$R^4$ is H or $CH_3$;
X is S, O or NH;
Y is a peptide having r independently selected amino acids, wherein at least one amino acid is selected from the group consisting of an unnatural amino acid and a D-amino acid;
Z is selected from the group consisting of radionuclide, biotin, a fluorophore, an antibody, horseradish peroxidase, an alkaline phosphatase, a chelating agent or a chelating agent-linker conjugate; and
r is an integer of from 3 to 20; and wherein said targeting conjugate binds to $\alpha_4\beta_1$ integrin with a binding constant of less than 10 micromolar, more preferably less than 10 nanomolar, and still more preferably less than 100 pM. In some of the most preferred embodiments, the targeting conjugate binds to $\alpha_4\beta_1$ integrin with a binding constant of less than 2 picomolar (pM).

In a further aspect, the present invention provides kits for imaging a tumor, organ, or tissue or for treating cancer, an inflammatory disease, or an autoimmune disease comprising one or more of the above-described compounds and directions for use in imaging or therapy.

IV. Compositions: $\alpha_4\beta_1$ Integrin Inhibitors

The $\alpha_4\beta_1$ integrin inhibitors of the present invention were identified using the "one-bead one-compound" (OBOC) combinatorial library method.

Combinatorial library methods not only offer great potential for facilitating the drug discovery process, but also provide powerful tools for basic research in various disciplines (Lam, Anti-Cancer Drug Design, 12:145-167 (1997); Tiebes, In "Comb. Chem." Ed. Weinheim, J. G. Wiley-VCH. pp. 1-34 (1999); Antonenko et al., Methods Princ. Med. Chem., 7:39-80 (2000); Lehn and Eliseev, Science, 291:2331-2332 (2001); Appell et al., Sep. Sci. Technol., 3:23-56 (2001)).

The OBOC combinatorial library method was first reported in 1991 (Lam et al., Nature, 354:82-84 (1991)). In essence, when a "split-mix" synthesis method (Lam et al., id; Houghten et al., Nature, 354:84-86 (1991); Furka et al., Int. J. Peptide Protein Res., 37:487-493 (1991)) is used to generate a combinatorial library, each bead expresses only one chemical entity (Lam et al., id; Lam et al., Chem. Rev., 97:411-448 (1997)). Random libraries of millions of beads can then be screened in parallel for a specific acceptor molecule (e.g., receptor, antibody, enzyme, virus, whole cell, etc.). Using an enzyme-linked colorimetric assay similar to that used in Western blotting, the OBOC combinatorial library method was successful in identifying ligands for an anti-β-endorphin antibody (Lam et al., Bioorg. Med. Chem. Lett., 3:419-424 (1993)), streptavidin (Lam et al., Pept.: Chem., Struct., Biol., Proc. Am. Pept. Symp. 13th, pp. 1005-1006 (1994)), avidin (Lam and Lebl, ImmunoMethods, 1:11-15 (1992)), anti-insulin monoclonal antibody recognizing a discontinuous epitope (Lam et al., In "Peptides: Chem., Struct., and Biol." Ed. Hodges, pp. 1003-1004 (1994)), MHC-Class 1 molecules (Smith et al., Mol. Immunol., 31:1431-1437 (1994)), indigo carmine (a small organic dye) (Lam et al., Drug Dev. Res., 33:157-160 (1994)), and surface idiotype of B-cell lymphoma cell lines (Lam et al., Biomed. Pept, Prot., and Nuc. Acids, 1:205-210 (1995)). The positive beads were then physically isolated for structural determination by microsequencing using automatic Edman degradation (Lam et al., Nature, 354:82-84 (1991)).

The OBOC combinatorial library method can also be used for screening radiolabeled peptides. For example, substrate motifs for protein kinases were identified using peptides radiolabeled with [$\gamma$-$^{32}$P]-ATP. (Lam and Wu, Methods, 6:401-403 (1994); Wu et al., Biochem., 33:14825-14833 (1994); Lam et al., Intl. J. Prot. Pept. Res., 45:587-592 (1995); Lou et al., Bioorg. Med. Chem., 4:677-682 (1996)). Using these peptide substrates as templates, potent pseudo-substrate-based peptide inhibitors for p60$^{c-src}$ protein tyrosine kinase were also developed (Alfaro-Lopez et al., J. Med. Chem., 41:2252-2260 (1998)). Since the OBOC combinatorial library method uses a parallel approach, each compound is spatially separated on individual beads, and multiple different peptide motifs can be identified (Wu et al., J. Comb. Chem. High-throughput screening (2002)). Recently, OBOC combinatorial peptidomimetic libraries were used to identify peptidomimetic substrates for the development of c-src inhibitors (Kamath et al., In "Peptides: the wave of the future." Proc. of Pept. Symp., Jun. 9-14, 2001).

Using 4-((N'-2-methylphenyl)ureido)-phenylacetyl-LDVP ("BIO-1211") as a template, various OBOC combinatorial peptidomimetic libraries containing both naturally-occurring amino acids, unnatural amino acids, and D-amino acids were designed to elucidate $\alpha_4\beta_1$ integrin ligands with increased affinity, specificity, and stability. In order to remove ligands with low to moderate binding affinity, the screening method was modified by incorporating BIO-1211 as a competitive ligand in solution. As a result, only those ligands with high affinity were completely covered by a monolayer of live lymphoid cancer cells. Cancer cell-binding affinity was performed on Jurkat T leukemia cells, Molt-4 leukemia cells, and/or fresh cancer cells obtained from acute lymphocytic leukemia patients. By using this method, $\alpha_4\beta_1$ integrin ligands with affinity significantly higher than that of BIO-1211 were identified. Furthermore, all of the ligands identified contained at least one unnatural α-amino acid, D-amino acid, or a combination thereof, a property that confers greater stability to the ligands upon administration. Therefore, these ligands have significantly better pharmacokinetic properties as well as cancer targeting properties compared to BIO-1211. Examples 2-8 provide a detailed description of the ligands identified from each of the various OBOC combinatorial peptidomimetic libraries.

In addition to their use as therapeutic agents for cancer, inflammatory diseases, and autoimmune diseases, the $\alpha_4\beta_1$ integrin ligands of the present invention are also suitable for use as imaging agents for imaging tumors, organs, and tissues. Preferably, the ligands are conjugated to an imaging moiety such as a radionuclide, a chelating agent, a fluorophore, an antibody, biotin, horseradish peroxidase, alkaline phosphatase, or a derivative thereof. One of ordinary skill in the art will appreciate other imaging moieties suitable for conjugation to the ligands of the present invention.

V. Methods of Administration

The ligands of the present invention have particular utility in human and veterinary imaging, therapeutic, and diagnostic applications. For example, the ligands can be used for imaging tumors and for treating cancer, inflammatory diseases, and autoimmune diseases.

Administration of the ligands of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Moreover, where injection is to treat a tumor, administration may be directly to the tumor and/or into tissues surrounding the tumor.

The compositions containing a ligand or a combination of ligands of the present invention may be administered repeatedly, e.g., at least 2, 3, 4, 5, 6, 7, 8, or more times, or the composition may be administered by continuous infusion. Suitable sites of administration include, but are not limited to, dermal, mucosal, bronchial, gastrointestinal, anal, vaginal, eye, and ear. The formulations may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a ligand or a combination of ligands.

Methods for preparing such dosage forms are known to those skilled in the art (see, for example, *Remington's Pharmaceutical Sciences*, 18TH ED., Mack Publishing Co., Easton, Pa. (1990)). The composition to be administered contains a quantity of the ligand or combination of ligands in a pharmaceutically effective amount for imaging a tumor, organ, or tissue or for relief of a condition being treated, when administered in accordance with the teachings of this invention. In addition, pharmaceutically acceptable salts of the ligands of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., *Remington's Pharmaceutical Sciences*, supra.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the ligands or combination of ligands, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The ligands can also be formulated into a suppository disposed, for example, in a polyethylene glycol (PEG) carrier.

Liquid compositions can be prepared by dissolving or dispersing a ligand or a combination of ligands and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The ligands of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the ligand to the appropriate site or sites. However, one of ordinary skill in the art understands that the dose administered will vary depending on a number of factors, including, but not limited to, the particular ligand or set of ligands to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the ligands of the present invention permits a wider margin of safety for dosage concentrations and for repeated dosing.

VI. Examples

The following examples are offered to illustrate, but not to limit, the claimed invention. A number of amino acids, analogs of amino acids and amino acid replacements are provided along with their abbreviations in the tables below and throughout the specification. One of skill in the art will appreciate that those abbreviations are also used for brevity in the attached claims. Peptide portions of the present invention can be prepared as described in co-pending application U.S. Ser. No. 11/140,548 filed May 26, 2005, incorporated herein by reference.

General Synthetic Procedures.

All chemicals were purchased from commercial suppliers and used without further purification. Rink amide resin (0.5 mmol/g loading, 100-200 mesh) was purchased from Tianjin Nankai Hecheng Sci & Tech. Co., Ltd, (batch number GRM-0406-J). Analytical TLC was carried out on pre-coated plates (silica gel 60, F254) and visualized with UV light. NMR spectra ($^1$H at 300 MHz, 400 MHz, 600 MHz; $^{13}$C at 75 MHz, 100 MHz) were recorded in DMSO-$d_6$, methanol-$d_4$, and acetone-$d_6$ as solvents and chemical shifts are expressed in parts per million relative to TMS. The specifications of the LC/MS are as follows: electrospray (+) ionization, mass range 100-900 Da, 20 V cone voltage, and Xterra® MS $C_{18}$ column (2.1 mm×50 mm×3.5 µm). CC refers to normal-phase silica-gel column chromatography. Concentration refers to rotary evaporation under reduced pressure. After each solid-phase step, the resin was washed by sequential treatment with the following solvents: DMF (2×5 mL), H$_2$O (2×5 mL), CH$_3$OH, (3×5 mL), and CH$_2$Cl$_2$ (5×5 mL).

Example 1

This example illustrates the preparation of intermediates, compounds and conjugates as generally provided in Schemes 1 and 2 (see FIGS. 1 and 2). Compound and intermediate numbering corresponds to that found in the noted Schemes.

Intermediates—Aryl Isocyanate Esters

General Procedure for Aryl Isothiocyanate Esters

Ethyl 4-Isothiocyanatobenzoate (2a)

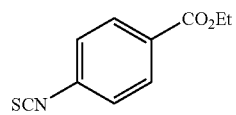

Following a previously reported procedure (see, R. D. Carpenter, et al., *J. Comb. Chem.* 2006, 8, 907), a solution of an appropriate aniline ester (4.5 g, 27.3 mmol) and triethylamine (60.1 mmol, 8.37 mL) in ethyl acetate (160 mL), was treated with thiophosgene (30.0 mmol, 2.30 mL) in ethyl acetate (130 mL) dropwise over 30 min at 0° C. After addition, the cooling bath was removed and the reaction mixture was allowed to gradually warm up to room temperature over 12 h. The workup consisted of diluting with ethyl acetate, followed by washing sequentially with water (200 mL×2) and brine (200 mL). The organic layer was dried (MgSO$_4$), concentrated, and the crude product was purified via short path CC (hexanes/ethyl acetate, 9:1) to give 2a (5.03 g, 89%). The analytical data are in accord with literature values (see, A. A. R. Sayigh, et al., *J. Org. Chem.* 1965, 30, 2465).

Ethyl 2-(4-Isothiocyanatophenyl)acetate (2b)

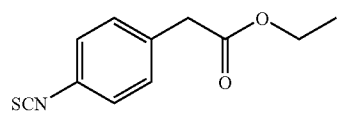

Following the General Procedure for Aryl Isothiocyanate Esters yielded 2b (5.20 g, 93%). The analytical data are in accord with literature values (see, D. W. Growne and G. W. Dyson, *J. Chem. Soc.* 1935, 178).

Methyl 3-(4-Isothiocyanatophenyl)propanoate (2c)

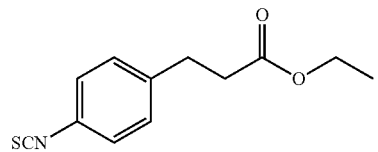

Following the General Procedure for Aryl Isothiocyanate Esters yielded 2c (5.41 g, 90%). The analytical data are in accord with literature values (see, R. D. Carpenter, et al., *J. Comb. Chem.* 2006, 8, 907).

Methyl 3-Isothiocyanatobenzoate (2d)

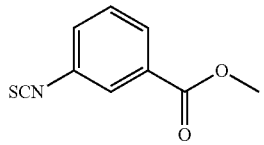

Following the General Procedure for Aryl Isothiocyanate Esters yielded 2d (7.06 g, 92% yield). The analytical data are in accord with literature values (see, M. Budesinsky, O. Exner. *Magn. Reson. Chem.* 1989, 27, 585).

Methyl 2-(4-Isothiocyanatophenyl)propionate (2e)

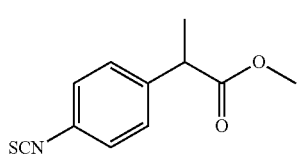

Following the General Procedure for Aryl Isothiocyanate Esters yielded 2e (4.11 g, 88%). The analytical data are in accord with literature values (see, R Pigula, et al., *Organika* 2003, 2001-2002, 11).

Intermediates—Heterocyclic Acids

General Procedure for Heterocyclic Acids 3-(1H-Benzo[d]imidazol-2-ylamino)benzoic Acid (3)

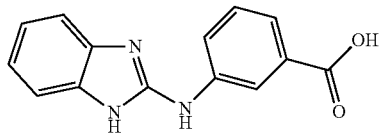 [SMILES: O=C(O)c1cccc(Nc2nc3ccccc3[nH]2)c1]

Following the General Procedure for Heterocyclic Acids yielded 3 (2.32 g, 88%). Following a previously reported procedure (see, R. D. Carpenter, et al., *J. Comb. Chem.* 2006, 8, 907), to a solution of o-phenylenediamine (1.76 g, 16.3 mmol) in $CH_2Cl_2$ (75 mL) was added a solution of the aryl isothiocyanate ester (For 2d, 3.0 g, 15.5 mmol) in $CH_2Cl_2$ (75 mL) dropwise over 30 min, followed by stirring for 16 h at room temperature. After TLC showed that the aryl isothiocyanate was consumed, the appropriate carbodiimide reagent [1,3-diisopropylcarbodiimide (DIC) or N-(3-dimethylaminopropyl)-N'-ethylcarbodiimide hydrochloride (EDCI)] was added (for 3, DIC (46.5 mmol, 7.2 mL)), and the reaction proceeded at room temperature until TLC showed the intermediate thiourea was consumed. In most instances, this was between 4-8 h., but in some cases this took as long as 16 h (3, 6 h). If DIC was employed (3) the concentrated crude product was recrystallized from hot $CHCl_3$ and petroleum ether to give the benzimidazole ester (3.67 g). If EDC was utilized, then the residue was taken up in ethyl acetate/$H_2O$ followed by washing ($H_2O$, brine), drying ($MgSO_4$), and concentration to give the benzimidazole ester (4.08 g) which was used without further purification. A solution of the benzimidazole ester (4.08 g, 15.3 mmol) in dioxane/$H_2O$ (125 mL/80 mL) was treated with LiOH (1.83 g, 76.4 mmol) and the solution was refluxed for 16 h. The reaction mixture was concentrated, and the residue was taken up in aqueous 2 M NaOH. This basic water layer (pH ~10) was washed twice with ether before being acidified with concentrated HCl to pH ~2-3 at which point 3 precipitated as a white solid (3.38 g, 86%). The analytical data are in accord with literature values (see, N. Chandrakumar, et al., U.S. Pat. No. 5,773,646 and *Chem. Abstr.* 1998, 72).

3-($5^6$-Bromo-1H-benzo[d]imidazol-2-ylamino)benzoic Acid (4)

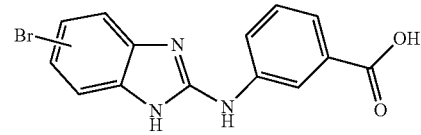

Following the General Procedure for Heterocyclic Acids yielded 4 (Yield 1.27 g, 78%). The analytical data are in accord with our previously reported values (see, R. D. Carpenter, et al., *J. Comb. Chem.* 2006, 8, 907).

3-(4-($5^6$-Bromo-1H-benzo[d]imidazol-2-ylamino)phenyl)propanoic Acid (5)

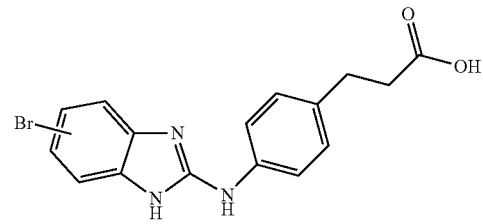

Following the General Procedure for Heterocyclic Acids yielded 5 (Yield 1.82 g, 83%). The analytical data are in accord with our previously reported values (see, R. D. Carpenter, et al., *J. Comb. Chem.* 2006, 8, 907).

4-($5^6$-Bromo-1H-benzo[d]imidazol-2-ylamino)benzoic Acid (6)

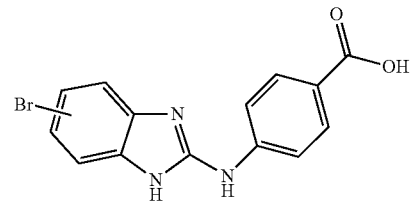

Following the General Procedure for Heterocyclic Acids yielded 6 (1.51 g, 79%). The analytical data are in accord with our previously reported values (see, R. D. Carpenter, et al., *J. Comb. Chem.* 2006, 8, 907).

2-(4-(1H-benzo[d]imidazol-2-ylamino)phenyl)propanoic acid (7)

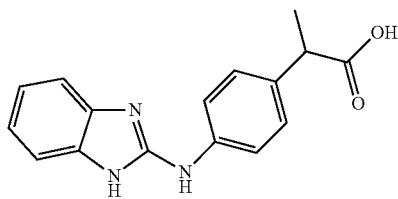 [SMILES: CC(C(=O)O)c1ccc(Nc2nc3ccccc3[nH]2)cc1]

Following the General Procedure for Heterocyclic Acids yielded 7 (2.05 g, 71%) as a light brown solid: mp 355-358° C.; IR (neat) 3550 (st, br), 3284 (sh), 3050 (st) 1705 (st); $^1$H NMR (300 MHz, DMSO-d$_6$): δ 7.66 (d, J=8.7 Hz, 2H), 7.31 (dd, J=5.7 Hz, J=3 Hz, 2H), 7.23 (d, J=8.7 Hz, 2H), 6.99 (dd, J=5.4 Hz, J=3 Hz, 2H), 3.62 (q, J=7.2 Hz, 1H), 1.34 (d, J=6.9 Hz, 3H); $^{13}$C NMR (75 MHz, DMSO-d$_6$): δ 175.7, 150.5, 139.1, 136.8, 133.9, 127.9, 127.9, 120.4, 117.7, 112.5, 44.1, 18.6; ESI MS (m/z) 282 (M+H)$^+$. Anal. Calcd for C$_{16}$H$_{15}$N$_3$O$_2$: C, 68.31; H, 5.37; N, 14.94. Found: C, 68.07; H, 5.36; N, 14.42. Purity was determined to be 98% by HPLC analysis on the basis of absorption at 220 nm.

2-(4-(5$^6$-Bromo-1H-benzo[d]imidazol-2-ylamino)phenyl)acetic Acid (8)

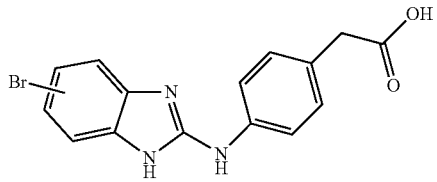

Following the General Procedure for Heterocyclic Acids yielded 8 (3.31 g, 79%). The analytical data are in accord with our previously reported values (see, R. D. Carpenter, et al., *J. Comb. Chem.* 2006, 8, 907).

2-(4-(1H-Benzo[d]imidazol-2-ylamino)phenyl)acetic Acid (9)

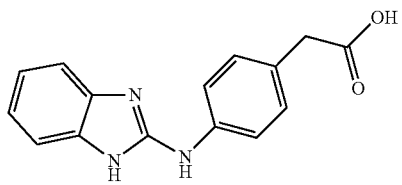 [SMILES: O=C(O)Cc1ccc(Nc2nc3ccccc3[nH]2)cc1]

Following the General Procedure for Heterocyclic Acids yielded 9 (4.82 g, 83%). The analytical data are in accord with our previously reported values (see, R. D. Carpenter, et al., *J. Comb. Chem.* 2006, 8, 907).

4-(5$^6$-methyl-1H-benzo[d]imidazol-2-ylamino)benzoic acid (10)

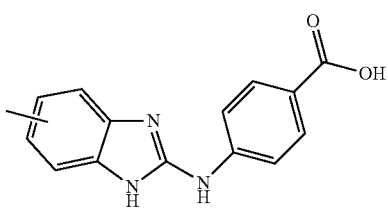

Following the General Procedure for Heterocyclic Acids yielded 10 (3.43 g, 74%) as a light gray solid: mp 368-370° C.; IR (neat) 3542 (st, br), 3284 (sh), 3050 (sh), 2984, 1699 (st); $^1$H NMR (300 MHz, DMSO-d$_6$): δ 7.97 (d, J=6.6 Hz, 2H), 7.58 (d, J=7.2 Hz, 2H), 7.35 (d J=7.8 Hz, 1H), 7.28 (s, 1H), 7.05 (d, J=8.1 Hz), 2.35 (s, 3H); $^{13}$C NMR (75 MHz, DMSO-d$_6$): δ 166.9, 146.6, 141.3, 133.1, 131.1, 130.6, 128.4, 126.6, 124.6, 120.1, 112.3, 112.1, 21.2; ESI MS (m/z) 268 (M+H)$^+$. Anal. Calcd for C$_{15}$H$_{13}$N$_3$O$_2$: C, 67.40; H, 4.90; N, 15.72. Found: C, 67.63; H, 4.91; N, 15.78. Purity was determined to be 99% by HPLC analysis on the basis of absorption at 220 nm.

3-(4-(1H-Benzo[d]imidazol-2-ylamino)phenyl)propanoic Acid (11)

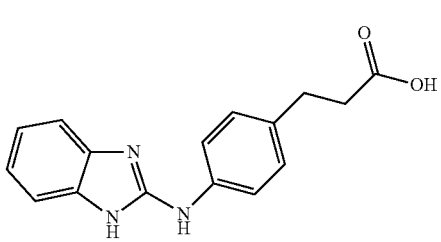 [SMILES: O=C(O)CCc1ccc(Nc2nc3ccccc3[nH]2)cc1]

Following the General Procedure for Heterocyclic Acids yielded 11 (1.51 g, 79%). The analytical data are in accord with our previously reported values (see, R. D. Carpenter, et al., *J. Comb. Chem.* 2006, 8, 907).

4-(1H-Benzo[d]imidazol-2-ylamino)benzoic Acid (12)

Following the General Procedure for Heterocyclic Acids yielded 12 (2.32 g, 88%). The analytical data are in accord with literature values (see, A Mohnsen, et al., *Pharmazie*, 1976, 31, 348).

4-(4-methyl-1H-benzo[d]imidazol-2-ylamino)benzoic acid (13)

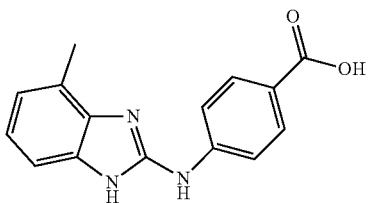 [SMILES: Cc1cccc2[nH]c(Nc3ccc(C(=O)O)cc3)nc12]

Following the General Procedure for Heterocyclic Acids yielded 13 (3.82 g, 82%) off white solid: mp 375-378° C.; IR (neat) 3534 (st, br), 3274 (sh), 3042 (sh), 2992, 1694 (st); $^1$H NMR (400 MHz, DMSO-d$_6$): δ 12.02 (br s, 1H), 7.99 (d, J=7.2 Hz, 2H), 7.62 (d, J=7.6 Hz, 2H), 7.37 (apparant d, J=8.4 Hz, 1H), 7.30 (apparent s, 1H), 7.07 (apparant d, J=8.4 Hz, 1H); 2.37 (s, 3H); $^{13}$C NMR (100 MHz, DMSO-d$_6$): δ 166.8, 146.6, 141.5, 132.9, 131.1, 130.8, 128.7, 126.3, 124.5, 124.4, 120.0, 112.4, 21.3; ESI MS (m/z) 268 (M+H)$^+$. Anal. Calcd for C$_{15}$H$_{13}$N$_3$O$_2$: C, 67.40; H, 4.90; N, 15.72. Found: C, 67.63; H, 4.90; N, 15.78. Purity was determined to be 97% by HPLC analysis on the basis of absorption at 220 nm.

2-(4-(benzo[d]thiazol-2-ylamino)phenyl)acetic acid (14)

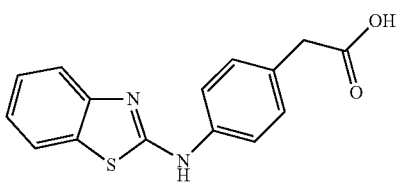 [SMILES: O=C(O)Cc1ccc(Nc2nc3ccccc3s2)cc1]

Following the General Procedure for Heterocyclic Acids yielded 14 (2.81 g, 70%). The analytical data are in accord with literature values (see, S, N. Sawhney, et al., *Indian J. Chem., Sect. B: Org. Chem. Ind Med. Chem.* 1978, 16B, 605).

2-(4-(4-methylbenzo[d]oxazol-2-ylamino)phenyl)acetic acid (15)

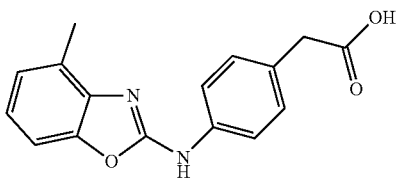 [SMILES: Cc1cccc2oc(Nc3ccc(CC(=O)O)cc3)nc12]

Following the General Procedure for Heterocyclic Acids yielded 15 (2.49 g, 75%) as a gray solid: mp 337-339° C.; IR (neat) 3539 (st, br), 3268 (sh), 3049 (sh), 2984, 1724 (st); $^1$1-1 NMR (400 MHz, DMSO-d$_6$): δ 10.56 (br s, 1H), 7.69 (d, J=6.8 Hz, 2H), 7.24 (apparant t, 3H), 7.02-6.95 (m, 2H), 3.50 (s, 2H), 2.47 (s, 3H); $^{13}$C NMR (100 MHz, DMSO-d$_6$): δ 172.9, 157.5, 146.6, 141.3, 137.5, 129.9, 128.6, 126.3, 124.7, 121.3, 117.5, 106.4, 22.5, 16.2; ESI MS (m/z) 283 (M+H)$^+$. Anal. Calcd for C$_{16}$H$_{14}$N$_2$O$_3$: C, 68.07; H, 5.00; N, 9.92.

Found: C, 68.18; H, 5.00; N, 9.95. Purity was determined to be 99% by HPLC analysis on the basis of absorption at 220 nm.

2-(4-(benzo[d]oxazol-2-ylamino)phenyl)acetic acid (16)

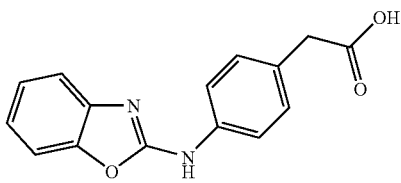 [SMILES: O=C(O)Cc1ccc(Nc2nc3ccccc3o2)cc1]

Following the General Procedure for Heterocyclic Acids yielded 16 (1.89 g, 79%). The analytical data are in accord with literature values (see, A. Nakayama, et al., Int. Patent JP 11641, 2002).

2-(4-(4-methyl-1H-benzo[d]imidazol-2-ylamino)phenyl)acetic acid (17)

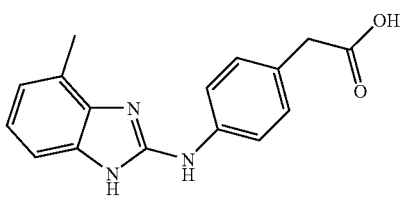 [SMILES: Cc1cccc2[nH]c(Nc3ccc(CC(=O)O)cc3)nc12]

Following the General Procedure for Heterocyclic Acids yielded 17 (3.55 g, 84%) as a light gray solid: mp 385-387° C.; IR (neat) 3547 (st, br), 3260 (sh), 3057 (sh), 2981, 1718 (st); $^1$H NMR (300 MHz, DMSO-d$_6$): δ 13.29 (br s, 1H), 11.38 (s, 1H), 7.42 (d, J=8.7 Hz, 2H), 7.37 (d, J=8.4 Hz, 2H), 7.27 (d, J=7.8 Hz, 1H), 7.16 (apparent t, J=7.8 Hz, 1H), 7.06 (d, J=7.2 Hz, 1H), 3.62, (s, 2H), 2.49 (s, 3H); $^{13}$C NMR (75 MHz, DMSO-d$_6$): δ 163.6, 138.9, 126.1, 123.7, 121.8, 120.7, 119.9, 115.7, 114.6, 113.3, 113.0, 100.5, 31.6, 7.7; ESI MS (m/z) 282 (M+H)$^+$. Anal. Calcd for C$_{16}$H$_{15}$N$_3$O$_2$: C, 68.31; H, 5.37; N, 11.37. Found: C, 68.17; H, 5.36; N, 11.34. Purity was determined to be 97% by HPLC analysis on the basis of absorption at 220 nm.

4-(4-methylbenzo[d]oxazol-2-ylamino)benzoic acid (18)

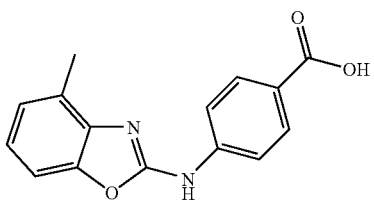 [SMILES: Cc1cccc2oc(Nc3ccc(C(=O)O)cc3)nc12]

Following the General Procedure for Heterocyclic Acids yielded 18 (1.67 g, 81%) as a light tan solid: mp 327-329° C.; IR (neat) 3560 (st, br), 3248 (sh), 3032 (sh), 2994, 1696 (st);

$^1$H NMR (300 MHz, DMSO-d$_6$): δ 11.11 (s, 1H), 7.96 (d, J=9 Hz, 2H), 7.91 (d, J=9 Hz, 2H), 7.26 (apparant t, 1H), 7.01-6.97 (m, 2H), 2.45 (s, 3H); $^{13}$C NMR (75 MHz, DMSO-d$_6$): δ 167.2, 156.9, 146.7, 143.1, 141.0, 130.8, 126.8, 124.8, 123.9, 121.9, 116.8, 106.6, 16.3; ESI MS (m/z) 269 (M+H)$^+$. Anal. Calcd for C$_{15}$H$_{12}$N$_2$O$_3$: C, 67.16; H, 4.51; N, 10.44. Found: C, 66.93; H, 5.34; N, 10.09. Purity was determined to be 99% by HPLC analysis on the basis of absorption at 220 nm.

4-(benzo[d]oxazol-2-ylamino)benzoic acid (19)

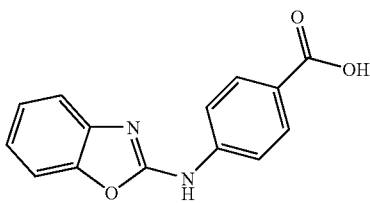 [SMILES: O=C(O)c1ccc(Nc2nc3ccccc3o2)cc1]

Following the General Procedure for Heterocyclic Acids yielded 19 (2.04 g, 76%). The analytical data are in accord with literature values (see, R Varma, *Current Science* 1976, 45, 53).

4-(benzo[d]thiazol-2-ylamino)benzoic acid (20)

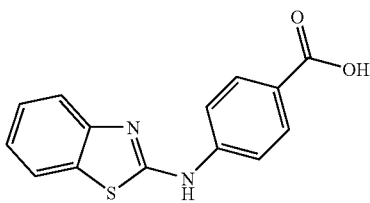 [SMILES: O=C(O)c1ccc(Nc2nc3ccccc3s2)cc1]

Following the General Procedure for Heterocyclic Acids yielded 20 (1.19 g, 85%). The analytical data are in accord with literature values (see, T. Tsubuki, et al., *Jpn. Kokai Tokkyo Koho* 258842, 2000).

2-(o-Tolylamino)-1H-benzo[d]imidazole-5$^6$-carboxylic Acid (21)

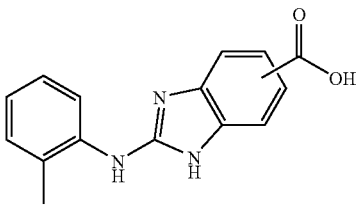

Following the General Procedure for Heterocyclic Acids yielded 21 (2.15 g, 80%). The analytical data are in accord with our previously reported values (see, R. D. Carpenter, et al., *J. Comb. Chem.* 2006, 8, 907).

Compound Coupling—Preparation of Peptide Component

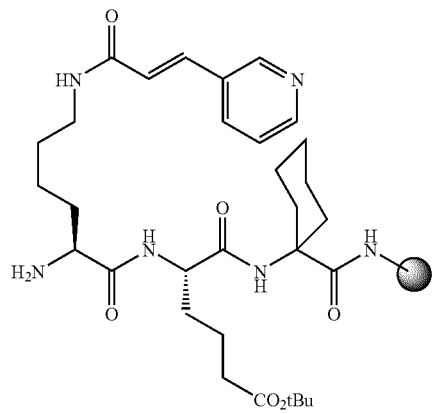 [SMILES: CNC(=O)C1(NC(=O)[C@H](CCCC(=O)OC(C)(C)C)NC(=O)[C@@H](N)CCCCNC(=O)/C=C/c2cccnc2)CCCCC1]

H$_2$N—K[(E)-3-(pyridin-3-yl)acrylamide]-Aad (OtBu)-Ach-Rink polystyrene (1)

Rink amide resin (2.35 g, 1.19 mmol) was swollen in DMF (30 mL) for 3 h, followed by treatment with 20% piperidine in DMF (20 mL). After washing, the resin was then treated with a pre-mixed solution of Fmoc-Ach-OH (Fmoc-Ach-OH; 1.30 g, 3.57 mmol), 1,3-diisopropylcarbodiimide (DIC; 3.57 mmol, 553 μL), and hydroxybenzotriazole (HOBt; 482 mg, 3.57 mmol) in DMF (20 mL) followed by shaking for 6 h. After a negative Kaiser test[21] washing, this sequence of deprotection/coupling was repeated thrice more with Fmoc-Aad(tBu)-OH (Fmoc-Aad(tBu)-OH; 1.57 g, 3.57 mmol), Dde-K(Fmoc)-OH (Dde-K(Fmoc)-OH; 1.85 g, 3.57 mmol), and (E)-3-(pyridin-3-yl)acrylic acid (532 mg, 3.57 mmol). After washing, the Dde-tripeptide resin was washed and treated with 2% H$_2$NNH$_2$ in DMF (20 mL) for 20 min, followed by washing to afford the free amino-tripeptide resin 1: IR (neat) 3430 (sh), 3370 (sh), 3084, 1740 (st), 1684 (st), 1680 (st), 1662 (st), 1654 (st) cm$^{-1}$.

Compound Coupling—Amide Formation with Carboxylic Acid

General Procedures for KLCA Analogs: (R)-5-(R)-2-(3-(1H-benzo[d]imidazol-2-ylamino)benzamido)-6-(E)-3-(pyridin-3-yl)acrylamido)hexanamido)-6-(1-carbamoylcyclohexylamino)-6-oxohexanoic acid (KLCA3)

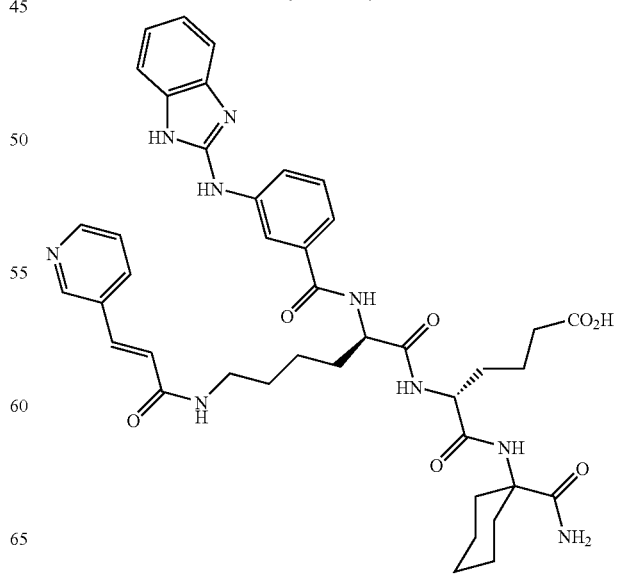

Heterocyclic acid 3 (253 mg, 0.180 mmol), 2-(1H-benzotriazole-1-yl)-1,1,3,3-tetramethyluronium hexafluorophosphate (HBTU; 67 mg, 0.180 mmol), and DIEA (54.7 mL, 0.360 mmol) were dissolved in DMF (3 mL) and the homogenous solution was allowed to stand for 10 min. This solution was then added to the free amino tripeptide resin 1 (120 mg, 0.06 mmol) and was shaken for 4 h. After washing, the resin was then cleaved with 3 mL of a 95:2.5:2.5 cleavage solution of TFA:H$_2$O:TIPS for 2 h, followed by draining and washing with the cleavage solution. This cleavage process was repeated once more, and the combined filtrates were concentrated under a gentle stream of nitrogen, precipitated with ether, centrifuged, and decanted. The precipitate was then purified by preparatory HPLC, and the combined fractions were lyophillized to afford KLCA3 (29 mg, 63% from Rink Amide resin) as a white powder: ESI MS (m/z) 780 (M+H)$^+$; EI HRMS (m/z) for C$_{41}$H$_{50}$N$_9$O$_7$: Calcd. 780.3828 (M+H)$^+$. Found: 780.3835. Purity was determined to be 99% by HPLC analysis on the basis of absorption at 220 nm.

The analytical data for KLCA3-21 as well as KLCA14-Cy5.5 are shown in Table 1.

TABLE 1

Overall yield from Rink amide resin, amount, purity, mass spectral data, and IC$_{50}$ of KLCA analogs.

| Compound | Yield[a] | Amount | Purity[b] | ESI MS[c] | EI HRMS | IC$_{50}$ |
|---|---|---|---|---|---|---|
| KLCA10 | 50% | 26 mg | 97% | 858, 860 | 858.2935 | 30 nM |
| KLCA11 | 54% | 29 mg | 98% | 886, 888 | 886.3253 | 379 nM |
| KLCA12 | 69% | 36 mg | 96% | 858, 860 | 858.2925 | 115 pM |
| KLCA13 | 44% | 21 mg | 95% | 794 | 794.3977 | 490 nM |
| KLCA14 | 62% | 30 mg | 100% | 811 | 811.3599 | 53 pM |
| KLCA15 | 74% | 36 mg | 99% | 809 | 809.3976 | 4 nM |
| KLCA16 | 69% | 33 mg | 100% | 795 | 795.3832 | 2 nM |
| KCLA17 | 61% | 29 mg | 99% | 795 | 795.3826 | 1 μM |
| KLCA18 | 64% | 30 mg | 100% | 781 | 781.3660 | 1 μM |
| KLCA19 | 58% | 28 mg | 100% | 797 | 797.3445 | 347 nM |
| KLCA14-Cy5.5 | 34% | 13 mg | 100% | — | 2242.7882[d] | — |

[a]Yield is calculated starting from Rink amide resin;
[b]Purity is measured by averaging two HPLC runs at different CH$_3$CN/H$_2$O gradients;
[c](M + H)$^+$.
[d]MALDI-TOF MS (M + Na)$^+$.

2-((1E,3E,5E)-5-(3-((R)-1-(1-((R)-2-((R)-2-(2-(4-(benzo[d]thiazol-2-ylamino)phenyl)acetamido)-6-((E)-3-(pyridin-3-yl)acrylamido)hexanamido)-5-carboxypentanamido)cyclohexyl)-27-carbamoyl-1,9,13,21,25,33-bexaoxo-5,17-dioxa-2,8,14,20,26,32-hexaazaheptatriacontan-37-yl)-1,1-dimethyl-6,8-disulfonato-1H-benzo[e] indol-2(3H)-ylidene)penta-1,3-dienyl)-3-ethyl-1,1-dimethyl-1H-benzo[e] indolium-6,8-disulfonate (KLCA14-Cy5.5)

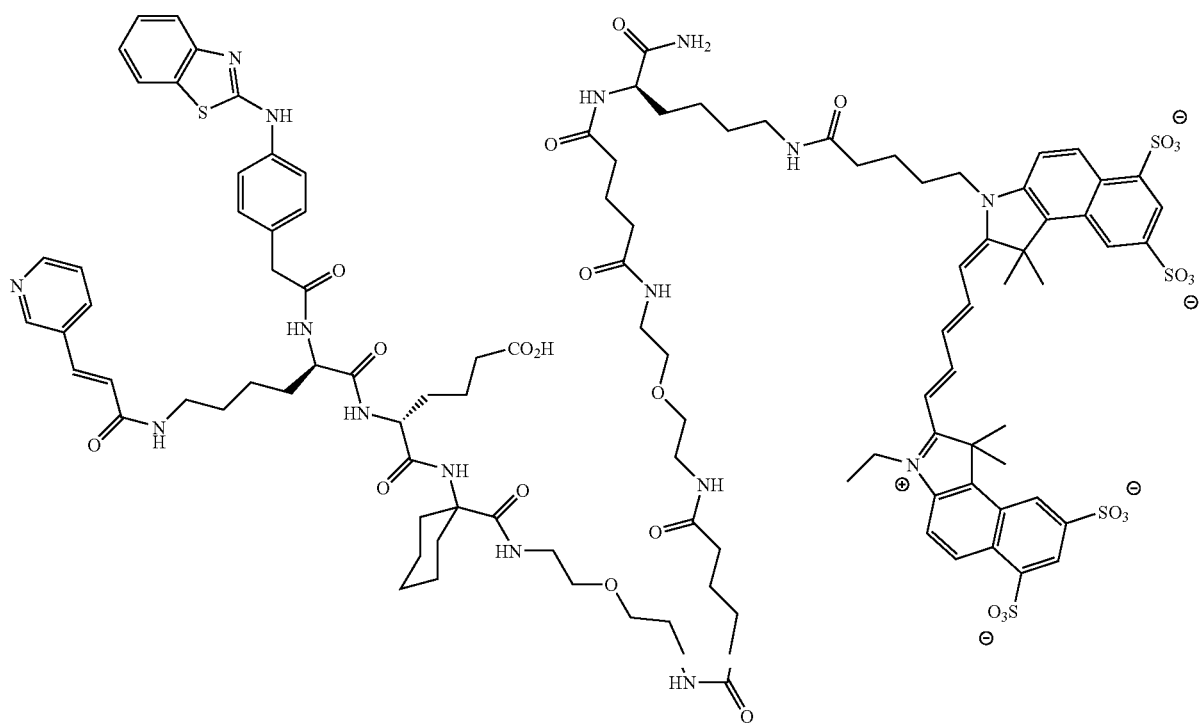

Rink amide resin (120 mg, 0.06 mmol) was swollen in DMF (3 mL) for 3 h, followed by treatment with 20% piperidine in DMF (20 mL). After washing, the resin was then treated with a pre-mixed solution of Fmoc-K(Dde)-OH (93 mg, 0.180 mmol), 1,3-diisopropylcarbodiimide (DIC; 0.180 mmol, 27.9 µL), and hydroxybenzotriazole (HOBt; 24.3 mg, 0.180 mmol) in DMF (3 mL) followed by shaking for 6 h. After a negative Kaiser test[21] washing, this sequence of deprotection/coupling was repeated twice with N-(Fmoc-8-amino-3,6-dioxa-octyl)succinamic acid (85 mg, 0.180 mmol), then Fmoc-Ach-OH (66 mg, 0.180 mmol), Fmoc-Aad(OtBu)-OH (79 mg, 0.180 mmol), Fmoc-K(Alloc)-OH (82 mg, 0.180 mmol). The free α-amino resin was then treated with a pre-mixed solution of 14 (51 mg, 0.180 mmol), HBTU (68 mg, 0.180 mmol), and DIEA (35.84, 0.180 mmol) in DMF (3 mL) for 4 h. After washing the c-Alloc protected amine was deprotected by treatment with a solution of Pd(PPh$_3$)$_4$ (11 mg, 9×10$^{-3}$ mmol) and phenylsilane (1.2 mmol, 149 µL) in DMF (3 mL) for 30 min. After draining and washing, this deprotection was repeated once more. This free ε-amino resin was then treated with a solution of (E)-3-(pyridin-3-yl)acrylic acid (27 mg, 0.180 mmol), DIC (0.180 mmol, 27.9 µL), and hydroxybenzotriazole (HOBt; 24.3 mg, 0.180 mmol) in DMF (3 mL). The ε-Dde protected amine was removed upon treatment of 2% H$_2$NNH$_2$ in DMF (3 mL) for 5 min, then washed with DMF and repeated for 15 min. After washing, to this free ε-amino resin was added Cy5.5-NHS (90 mg, 0.090 mmol) and DIEA (0.090 mmol, 15.8 µL) in DMF (3 mL) and allowed to shake for 8 h. After washing, the resin was then cleaved with 3 mL of a 95:2.5:2.5 cleavage solution of TFA:H$_2$O:TIPS for 2 h, followed by draining and washing with the cleavage solution. This cleavage process was repeated once more, and the combined filtrates were concentrated under a gentle stream of nitrogen, precipitated with ether, centrifuged, and decanted. The precipitate was then purified by preparatory HPLC, and the combined fractions were lyophillized to afford KCLCA14-Cy5.5 (13 mg, 34%) as a blue powder: ESI MS (m/z) 2221 (M+H)$^+$; ESI HRMS (m/z) for C$_{106}$H$_{131}$N$_{16}$NaO$_{25}$S$_5$: Calcd. 2242.7882 (M+Na)$^+$. Found: 2242.7871. Purity was determined to be 100% by HPLC analysis on the basis of absorption at 220 nm.

Example 2

This example provides amino acid descriptions for various peptide portions for the compounds and conjugates of the present invention. Peptides with the noted sequences, or using the indicated amino acids can be prepared as outlined above (using solid phase resins) or can be prepared using standard amino acid synthesis protocols. One of skill in the art will appreciate that various functional groups can require protecting groups through the course of synthesis.

TABLE 1

The 45 amino acids occurring at position Y$^4$ for those embodiments in which Y is a tetrapeptide having the formula —Y$^1$—Y$^2$—Y$^3$—Y$^4$.

| No. | Amino acid |
|---|---|
| 1 | D-Asp |
| 2 | Acpc |
| 3 | D-Asn |
| 4 | D-Ser |
| 5 | D-Gln |
| 6 | D-Thr |
| 7 | HoSer |
| 8 | Gly |
| 9 | D-Glu |
| 10 | HoCit |
| 11 | Hyp |
| 12 | D-His |
| 13 | Aad |
| 14 | D-Ala |
| 15 | 4-Pal |
| 16 | D-3-Pal |
| 17 | Acdt |
| 18 | Ahch |
| 19 | Akch |
| 20 | D-Tyr |
| 21 | Aib |
| 22 | D-Pro |
| 23 | D-Met |
| 24 | D-Val |
| 25 | Nva |
| 26 | D-Thi |
| 27 | D-Trp |
| 28 | Tyr(Me) |
| 29 | Phg |
| 30 | D-Phe |
| 31 | D-Ile |
| 32 | Ach |
| 33 | Tyr(diBr) |
| 34 | Nle |
| 35 | D-Phe(4-Me) |
| 36 | Tyr(di I) |
| 37 | Aic |
| 38 | Phe(3-Cl) |
| 39 | D-HoPhe |
| 40 | Chg |
| 41 | D-Bpa |
| 42 | D-Nal-2 |
| 43 | Ana |
| 44 | D-Phe(diCl) |
| 45 | Cha |

The D-stereoisomer of natural amino acid is designated by the standard three-letter code. Other abbreviations: Aad, α-aminohexanedioic acid; Acdt, 4-amino-4-carboxy-1,1-dioxo-tetrahydrothiopyran; Ach, 1-amino-1-cyclohexane carboxylic acid Acpc, 1-aminocyclopropane-1-carboxylic acid; Ahch, 1-amino-1-(4-hydroxycyclohexyl) carboxylic acid; Aic, 2-aminoindane-2-carboxylic acid; Aib, α-aminoisobutyric acid; Akch, 1-amino-1-(4-keto-cyclohexyl)carboxylic acid; Ana, 2-amino-2-naphthylacetic acid; D-Bpa, D-4-benzoylphenylalanine; Bta, benzothienylalanine; Cha, cyclohexylalanine; Chg, α-cyclohexylglycine; Dpr, α,β-diaminopropionic acid; DPTU, diphenylthiourea; HoCit, Homocitrulline; D-HoPhe, D-homophenylalanine; HoSer, Homoserine; Hyp, hydroxy proline; D-Nal-2, D-3-(2-Naphthyl)alanine; Nle, norleucine; Nva, norvaline; D-3-Pal, D-3-(3-pyridyl)alanine; 4-Pal, D-3-(4-pyridyl)alanine; Phe(3-Cl), 3-chlorophenylalanine; D-Phe(di Cl), D-3,4-dichlorophenylalanine; D-Phe(4-Me), D-4-methylphenylalanine; Phg, phenylglycine; D-Thi, D-3-(2-thienyl)alanine; Tyr(Me), O-methyltyrosine; Tyr(diBr), 3,5-dibromotyrosine; Tyr(diI), 3,5-diiodotyrosine.

TABLE 2

The 18 hydrophobic amino acids occurring at position Y$^3$ for those embodiments in which Y is a tetrapeptide having the formula —Y$^1$—Y$^2$—Y$^3$—Y$^4$.

| No. | Y$^3$ | Structure |
|---|---|---|
| 1 | Ile | H$_2$N—CH(—)—COOH |
| 2 | Aib | H$_2$N—C(—)(—)—COOH |
| 3 | Abu | H$_2$N—CH(—)—COOH |

TABLE 2-continued

The 18 hydrophobic amino acids occurring at position $Y^3$ for those embodiments in which Y is a tetrapeptide having the formula —$Y^1$—$Y^2$—$Y^3$—$Y^4$.

| No. | $Y^3$ | Structure |
|---|---|---|
| 4 | Leu | 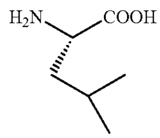 |
| 5 | Pra | 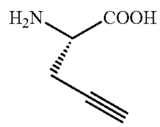 |
| 6 | Chg | 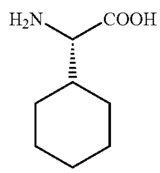 [SMILES: N[C@H](C(=O)O)C1CCCCC1] |
| 7 | Nva | 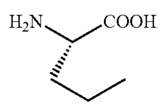 |
| 8 | Phg | 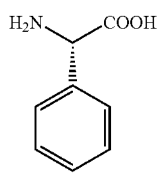 [SMILES: N[C@H](C(=O)O)c1ccccc1] |
| 9 | Cha | 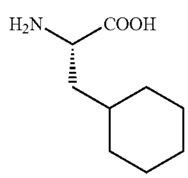 |
| 10 | Val | 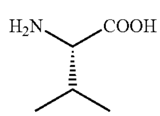 |
| 11 | Acpc | 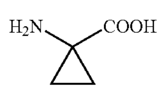 |
| 12 | Ala | 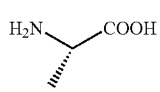 |
| 13 | Nle | 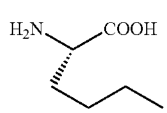 |
| 14 | Bug | 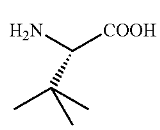 |
| 15 | Hle | |
| 16 | Phe | |
| 17 | HoPhe | |
| 18 | Tyr | |

TABLE 3

The 3 negatively charged amino acids occurring at position $Y^2$ for those embodiments in which Y is a tetrapeptide having the formula —$Y^1$—$Y^2$—$Y^3$—$Y^4$.

| No. | $Y^2$ | Structure |
|---|---|---|
| 1 | Asp | 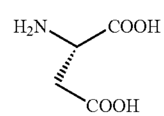 |
| 2 | Glu | 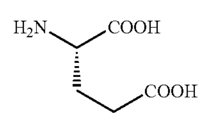 |
| 3 | Aad | 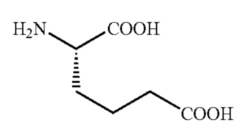 [SMILES: N[C@@H](CCCC(=O)O)C(=O)O] |

TABLE 4

The 6 hydrophobic amino acids occurring at position $Y^1$ for those embodiments in which Y is a tetrapeptide having the formula —$Y^1$—$Y^2$—$Y^3$—$Y^4$.

| No. | $Y^1$ | Structure |
|---|---|---|
| 1 | Nle | H₂N-CH(COOH)-CH₂CH₂CH₂CH₃ |
| 2 | Leu | H₂N-CH(COOH)-CH₂CH(CH₃)₂ |
| 3 | Pra | H₂N-CH(COOH)-CH₂C≡CH |
| 4 | HLe | H₂N-CH(COOH)-CH₂CH₂CH(CH₃)₂ |
| 5 | Cpa | H₂N-CH(COOH)-cyclopropyl |
| 6 | Cha | H₂N-CH(COOH)-CH₂-cyclohexyl |

TABLE 5

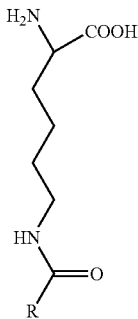

The 20 lysine derivatives occurring at position $Y^1$ for those embodiments in which Y is a tetrapeptide having the formula —$Y^1$—$Y^2$—$Y^3$—$Y^4$.

| $Y^1$ | R group | Structure |
|---|---|---|
| Lys27 | L-Pyroglutamic acid | (pyroglutamyl) |
| Lys73 | trans-4-Cotinine carboxylic acid | (cotinine carboxyl) |
| Lys55 | Levulinic acid | (levulinoyl) |
| Lys28 | Boc-1-amino cyclopropane-1-carboxlic acid | (aminocyclopropanecarbonyl) |
| Lys72 | 2-Pyrazine carboxylic acid | (pyrazine-2-carbonyl) |
| Lys12 | 3-Pyridine propionic acid | (3-pyridylpropanoyl) |
| Lys38 | trans-3-(3-Pyridyl)acrylic acid | (3-pyridylacryloyl) |
| Lys123 | Butyric acid | (butanoyl) |
| Lys63 | 3-Oxo-1-indancarboxylic acid | (3-oxoindanyl carbonyl) |
| Lys124 | Valeric acid | (pentanoyl) |

TABLE 5-continued

| | | |
|---|---|---|
| Lys82 | (S)-(+)-Oxo-4-phenyl-3-oxazolidineacetic acid | 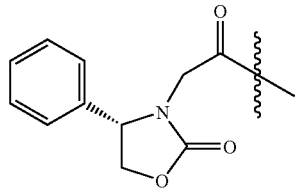 [SMILES: *C(=O)CN1C(=O)OC[C@@H]1c1ccccc1] |
| Lys31 | Boc-D-Tic | 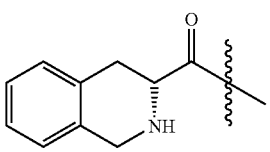 |
| Lys15 | 4-(Dimethylamino)phenylacetic acid | 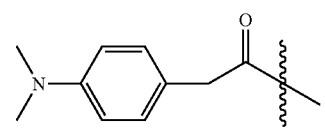 |
| Lys125 | Hexanoic acid | 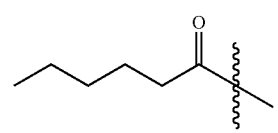 [SMILES: *C(=O)CCCCC] |
| Lys43 | Phenylpropionic acid | 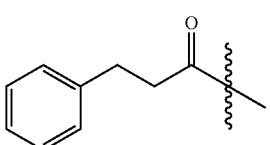 |
| Lys24 | 4-Chlorophenylacetic acid | 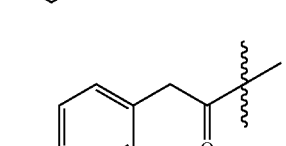 |
| Lys5 | Bromophenylacetic acid | 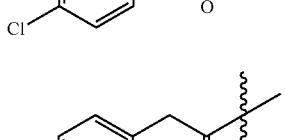 |
| Lys4 | 1-Naphthylacetic acid | 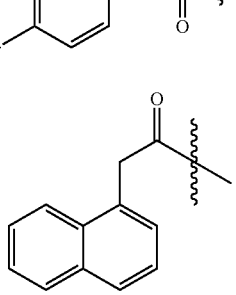 |
| Lys50 | 2-Phenoxybutyric acid | 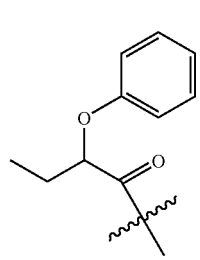 [SMILES: *C(=O)C(CC)Oc1ccccc1] |

TABLE 5-continued

| | | |
|---|---|---|
| Lys81 | 2,4-Dichlorophenyl-acetic acid | 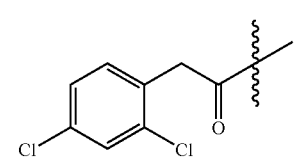 [SMILES: *C(=O)Cc1ccc(Cl)cc1Cl] |

Additionally, the homolysine compounds are those lysine derivatives above in which the side chain has an additional methylene (CH$_2$) unit. As a result, the amino acid described herein as, for example, Hly50 is the same as Lys50, with the addition of the methylene portion in the side chain and prior to the c-amino group (as is present in lysine).

TABLE 8

The 6 proline analogs occurring at position $Y^4$ for those embodiments in which Y is a tetrapeptide having the formula —$Y^1$—$Y^2$—$Y^3$—$Y^4$

| No. | $Y^4$ | Structure |
|---|---|---|
| 1 | Pro | 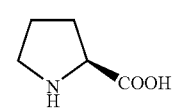 |
| 2 | Hyp | 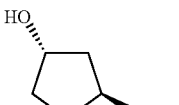 |
| 3 | Thz | 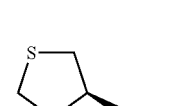 |
| 4 | Acp | 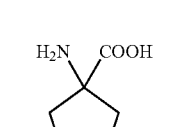 |
| 5 | Hyp(Bzl) | 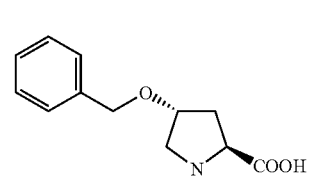 |
| 6 | Ppca | 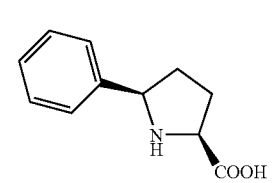 [SMILES: O=C(O)[C@@H]1CC[C@H](c2ccccc2)N1] |

TABLE 9
The 26 hydrophobic amino acids occurring at position $Y^3$ for those embodiments in which Y is a tetrapeptide having the formula —$Y^1$—$Y^2$—$Y^3$—$Y^4$
| No | $Y^3$ | Structure |
|----|-------|-----------|
| 1 | Ile | 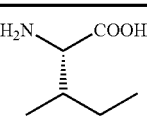 |
| 2 | Ala | 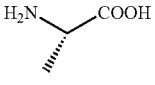 |
| 3 | Abu | 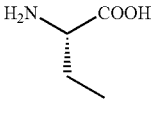 |
| 4 | Leu | 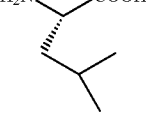 |
| 5 | Pra | 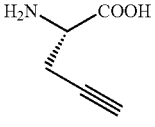 |
| 6 | Chg | 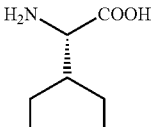 |
| 7 | Nva | 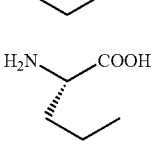 |
| 8 | Phg | 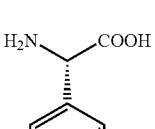 |
| 9 | Cha | 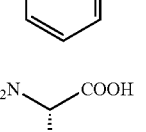 |
| 10 | Ach | 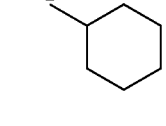 |
| 11 | Ppca | 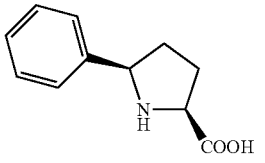 |
| 12 | Ana | 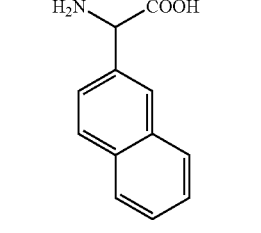 |
| 13 | Bpa | 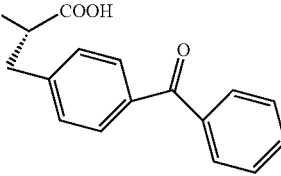 |
| 14 | Val | 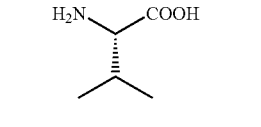 |
| 15 | Acpc |  |
| 16 | Thi | 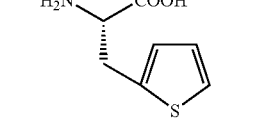 |
| 17 | Nle | 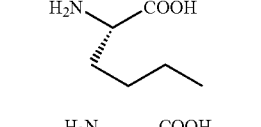 |
| 18 | D-Nal-2 | 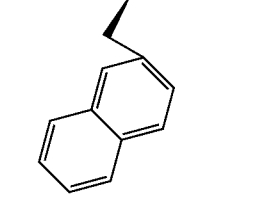 |
| 19 | Aic | 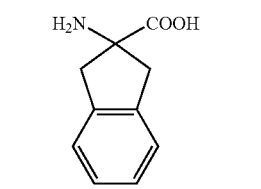 |

TABLE 9-continued

The 26 hydrophobic amino acids occurring at position $Y^3$ for those embodiments in which Y is a tetrapeptide having the formula —$Y^1$—$Y^2$—$Y^3$—$Y^4$

| No | $Y^3$ | Structure |
|---|---|---|
| 20 | D-Phe | 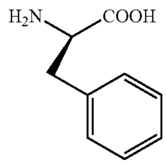 [SMILES: N[C@H](Cc1ccccc1)C(=O)O] |
| 21 | HoPhe | 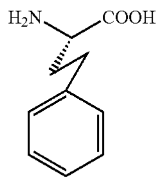 [SMILES: N[C@@H](CCc1ccccc1)C(=O)O] |
| 22 | Tyr | 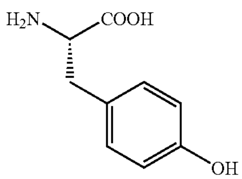 [SMILES: N[C@@H](Cc1ccc(O)cc1)C(=O)O] |
| 23 | Tyr(Me) | 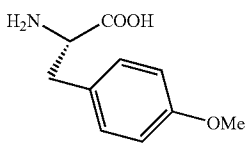 [SMILES: COc1ccc(C[C@H](N)C(=O)O)cc1] |
| 24 | Phe(3-Cl) | 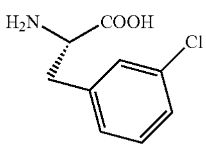 [SMILES: N[C@@H](Cc1cccc(Cl)c1)C(=O)O] |
| 25 | Tyr(diI) | 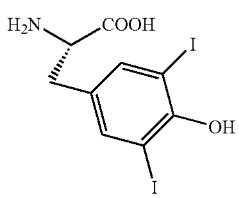 [SMILES: N[C@@H](Cc1cc(I)c(O)c(I)c1)C(=O)O] |
| 26 | Phe(4-Me) | 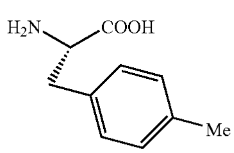 [SMILES: Cc1ccc(C[C@H](N)C(=O)O)cc1] |

TABLE 10

The 10 amino acids occurring at position $Y^1$ for those embodiments in which Y is a tetrapeptide having the formula —$Y^1$—$Y^2$—$Y^3$—$Y^4$

| No. | $Y^1$ | Structure |
|---|---|---|
| 1 | Nle | |
| 2 | Leu | 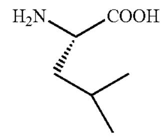 |
| 3 | HoPhe | 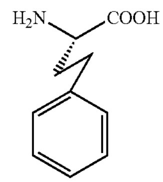 [SMILES: N[C@@H](CCc1ccccc1)C(=O)O] |
| 4 | Pra | 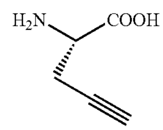 |
| 5 | Lys38 | 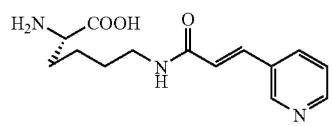 [SMILES: N[C@@H](CCCCNC(=O)/C=C/c1cccnc1)C(=O)O] |
| 6 | Hle | 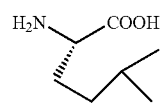 |
| 7 | Cpa | 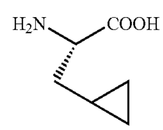 |
| 8 | Cha | 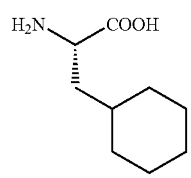 [SMILES: N[C@@H](CC1CCCCC1)C(=O)O] |
| 9 | Lys12 | 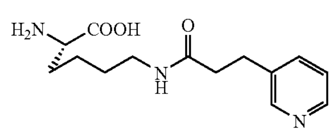 [SMILES: N[C@@H](CCCCNC(=O)CCc1cccnc1)C(=O)O] |
| 10 | Lys43 | 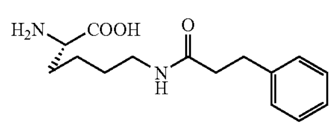 [SMILES: N[C@@H](CCCCNC(=O)CCc1ccccc1)C(=O)O] |

The ligands identified from this library have the following features: (1) hydrophobic amino acids such as leucine and leucine analogs (i.e., Nle, Hle, Cpa, Cha), and lysine derivatives such as Lys38 are preferred at position $Y^1$; (2) negatively charged amino acids such as Aad, Asp, and Glu are preferred at position $Y^2$; (3) hydrophobic amino acids are preferred at position $Y^3$; (4) proline analogs (i.e., Hyp), hydrophobic amino acids, and negatively charged amino acids are preferred at position $Y^4$.

Example 3

Cell Adhesion Assay Introduction $\alpha_4\beta_1$ integrins are cell surface heterodimeric glycoproteins that mediate cell adhesion to vascular cell adhesion molecule-1 (VCAM-1 or CD 106) as well as to extracellular matrix (ECM) protein fibronectin (FN). Integrin expression and function depend on cell activation. The dynamic changes in integrin affinity, avidity, or activation state are implicated in cell migration, survival and apoptosis, cancer development and metastasis. Binding affinities (IC50s) of the ligands were studied in a Molt4 T-cell leukemia adhesion assay by inhibiting the $\alpha_4\beta_1$-mediated cell adhesion to CS-1 peptide (DELPQLVTLPHPNLHGPEILDVPST), which is the binding motif of fibronectin to $\alpha_4\beta_1$ receptor.

General Procedure for Cell Adhesion Assay:

96-well plates were prepared by coating them with 5 μg/mL neutravidin for a one-hour period, followed by adding 2 ₋ μM biotin-conjugated CS-1 peptide. The wells were then blocked with 1% bovine serine albumin in phosphate buffer saline (PBS) solution, followed by adding a volume of 80 μL consisted of $1.3 \times 10^5$ Molt4 cells, and finally different dilutions of tested ligands in binding buffer (1 mM $Mn^{2+}$ TBS), were added to each well. To allow binding, the plates were incubated for 30 min at 37° C., followed by washing of unbound cells with PBS. Bound cells were fixed with 10% formalin buffered in phosphate for 30 min and stained with 0.5% crystal violet. After washing and drying at room temperature, the dye was dissolved in 1% SDS, and absorbance at 570 nm was measured using a 96-well TECAN OD UV/Vis spectrophotometer. Inhibition was calculated as a percentage resulting from the concentration-dependent curve.

Example 4

Xenograft Methods

Four to six week old male and female athymic nude (Nu/Nu) mice were purchased from Harlan Sprague Dawley (Indianapolis, Ind.). Mice were housed in the animal facility and fed ad lib with rodent pellets and water. Tumor xenografts were created by injecting Molt-4 (T-cell lymphoma) and/or Raji (B-cell lymphoma) ($1 \times 10^7$ cells in 200 μl incomplete RPMI media) subcutaneously on the right side and A549 ($1 \times 10^6$ cells in 200 μl incomplete DMEM media) subcutaneously on the left side under mild inhalation anesthesia (Halothane). Studies commenced when xenografts reached between 10-15 mm. All procedures were conducted under an approved protocol according to guidelines specified by the National Institute of Health Guide for Animal Use and Care.

Animals were anesthetized intraperitoneally with Nembutal (1 μL/g body wt) of 6 mg/mL Pentobarbitol. The tails were dilated with warm water and animal were injected iv. Animals were imaged serially for tumor uptake and washout. Duration of scan was 30 sec for each acquired exposure.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having a formula selected from:

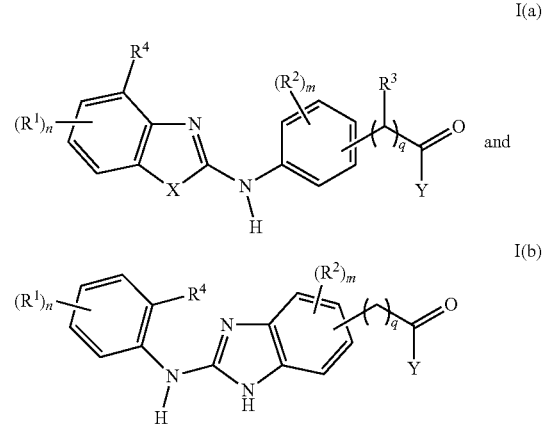

wherein the subscripts n, m and q are each independently selected integers of from 0 to 2;

$R^1$ is selected from the group consisting of hydrogen, halogen, $C_1$-$C_4$ alkyl, $C_1$-$C_4$ alkoxy, and $C_1$-$C_4$ haloalkyl;

$R^2$ is selected from the group consisting of hydrogen, halogen, $C_1$-$C_4$ alkyl and $C_1$-$C_4$ alkoxy;

$R^3$ is selected from the group consisting of hydrogen, $C_1$-$C_4$ alkyl and $C_3$-$C_8$ cycloalkyl;

$R^4$ is H or $CH_3$;

X is S, O or NH;

Y is a peptide having r independently selected amino acids, wherein at least one amino acid is selected from the group consisting of an unnatural amino acid and a D-amino acid; and r is an integer of from 3 to 20.

2. A compound of claim 1, having formula I(a).

3. A compound of claim 1, having formula I(b).

4. A compound of claim 1, wherein q is 0 and the portion bonded to Y is selected from the group consisting of:

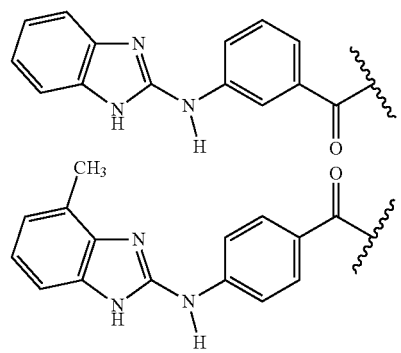

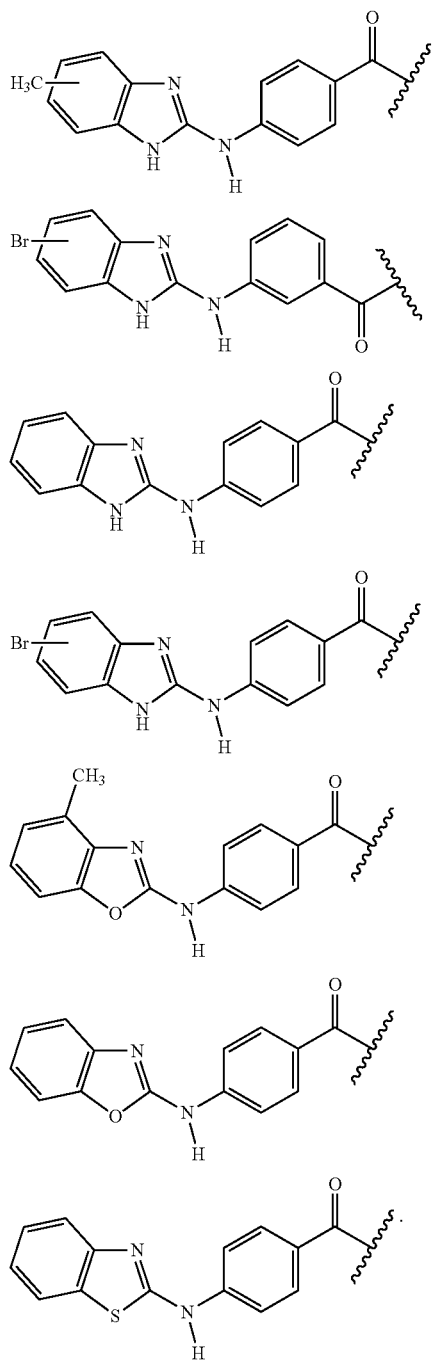
5. A compound of claim 1, wherein q is 1 and the portion bonded to Y is selected from the group consisting of:
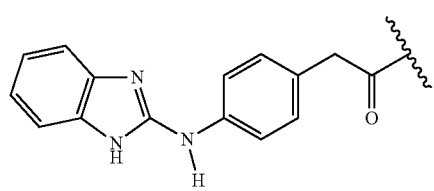
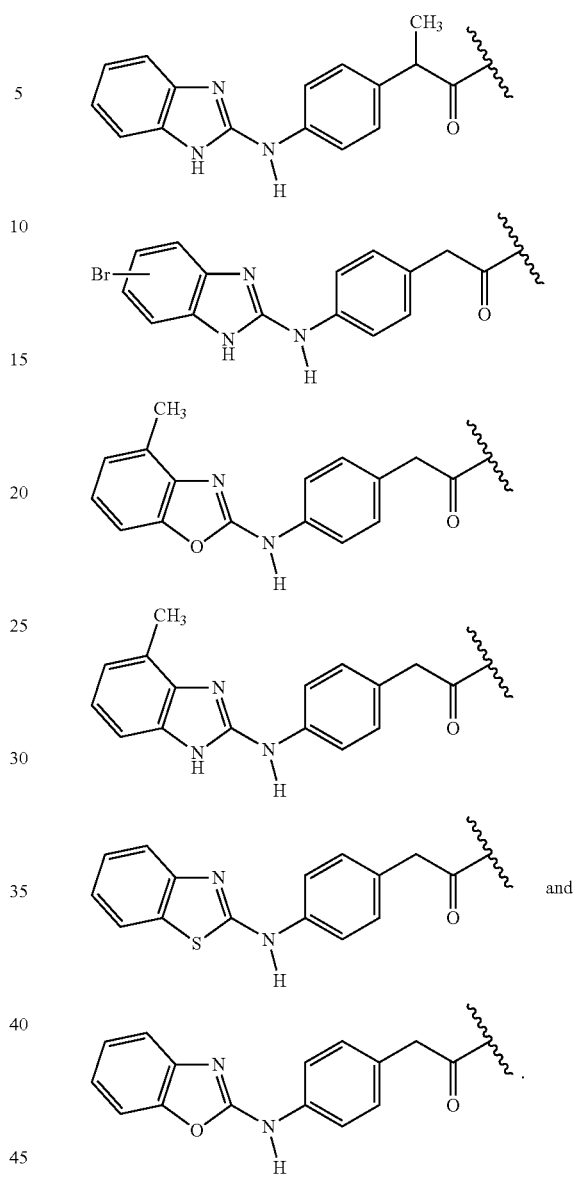
6. A compound of claim 1, wherein q is 2 and the portion bonded to Y is selected from the group consisting of:
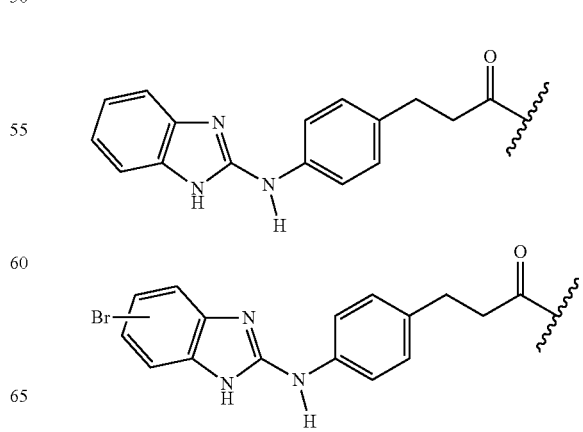

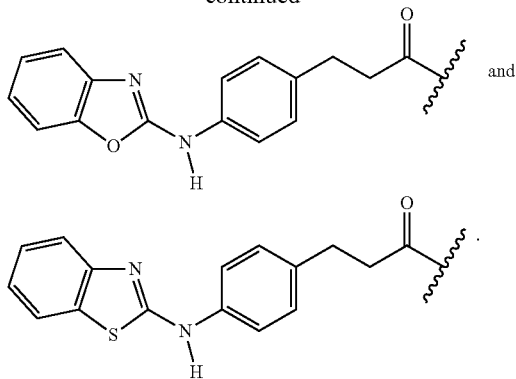

7. A compound in accordance with claim 1, wherein said unnatural amino acid is selected from the group consisting of an amino acid analog, amino acid mimetic, synthetic amino acid, N-substituted glycine, N-methyl amino acid, stereoisomers thereof, and combinations thereof.

8. A compound in accordance with claim 1, wherein said unnatural amino acid is selected from the group consisting of 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-acid (Dpr), α,γ-diaminopropionic acid (Dbu), α-tert-butylglycine (Bug), 3,5-dinitrotyrosine (Tyr(3,5-diNO$_2$)), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), homolysine (Hly), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo[3,2-a]pyridine-3-carboxylic acid (Btd), 3-aminobenzoic acid (3-Abz), 3-(2-thienyl)alanine (2-Thi), 3-(3-thienylalanine (3-Thi), α-aminooctanedioc acid (Asu), diethylglycine (Deg), 4-amino-4-carboxy-1,1-dioxotetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S,5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz (2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, homolysine (Hly), ornithine (Orn) and α,γ-diaminobutyric acid (Dbu), stereoisomers thereof, and combinations thereof.

9. A compound in accordance with claim 8, wherein said phenylalanine analog is selected from the group consisting of homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-diOMe)), 3,4-difluorophenylalanine (Phe(3,4-diF)), 3,5-difluorophenylalanine (Phe(3,5-diF)), 2,4-dichlorophenylalanine (Phe(2,4-diCl)), 3,4-dichlorophenylalanine (Phe(3,4-diCl)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe(F$_5$)), 3,4,5-trifluorophenylalanine (Phe(F$_3$)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr (Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

10. A compound in accordance with claim 8, wherein said derivatives of lysine (Lys), Orn and Dbu are selected from the group consisting of Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Hly38, Hly27, Hly73, Hly55, Hly28, Hly72, Hly12, Hly123, Hly63, Hly124, Hly82, Hly31, Hly15, Hly125, Hly43, Hly24, Hly5, Hly4, Hly50, Hly81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof.

11. A compound in accordance with claim 1, wherein said D-amino acid is selected from the group consisting of a D-α-amino acid, a D-β-amino acid, a D-γ-amino acid, and combinations thereof.

12. A compound in accordance with claim 11, wherein said D-α-amino acid is selected from the group consisting of a stereoisomer of a naturally-occurring α-amino acid, an unnatural D-α-amino acid, and combinations thereof.

13. A compound in accordance with claim 12, wherein said stereoisomer of a naturally-occurring α-amino acid is selected from the group consisting of D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

14. A compound in accordance with claim 1, wherein r is an integer of from 3 to 7.

15. A compound in accordance with claim 1, wherein Y is a tetrapeptide having the following structure:

$$-Y^1-Y^2-Y^3-Y^4,$$

wherein
  $Y^1$ is selected from the group consisting of a hydrophobic amino acid and derivatives of lysine, homolysine (Hly), ornithine (Orn) and α,γ-diaminobutyric acid (Dbu);
  $Y^2$ is a negatively charged amino acid;
  $Y^3$ is a hydrophobic amino acid; and
  $Y^4$ is selected from the group consisting of a naturally-occurring amino acid, an unnatural amino acid, and a D-amino acid.

16. A compound in accordance with claim 15, wherein $Y^4$ has a carboxyl-terminal group selected from the group consisting of an amide group and a carboxylic acid group.

17. A compound in accordance with claim 15, wherein said hydrophobic amino acid is independently selected from the group consisting of leucine (Leu), a leucine analog, phenylalanine (Phe), a phenylalanine analog, proline (Pro), a proline analog, valine (Val), isoleucine (Ile), glycine (Gly), alanine (Ala), norvaline (Nva), 1-aminocyclopropane-1-carboxylic acid (Acpc), 1-aminocyclobutane-1-carboxylic acid (Acb), α-cyclohexylglycine (Chg), α-aminoisobutyric acid (Aib), α-aminobutyric acid (Abu), 3-(2-thienyl)alanine (2-Thi), 3-(3-thienylalanine (3-Thi), 3-(3-pyridyl)alanine (3-Pal), 3-(2-naphthyl)alanine (Nal-2), 2-amino-2-naphthylacetic acid (Ana), 3,5-dinitrotyrosine (Tyr(3,5-diNO$_2$)), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 2-aminoindane-2-carboxylic acid (Aic), (2S,5R)-5-phenylpyrrolidine-2-carboxylic acid (Ppca), 4-thiazoylalanine (Tha), 2-aminooctanoic acid (Aoa), 2-aminoheptanoic acid (Aha), and stereoisomers thereof.

18. A compound in accordance with claim 17, wherein said leucine analog is selected from the group consisting of norleucine (Nle), homoleucine (Hle), propargylglycine (Pra), cyclopropylalanine (Cpa), cylobutylalanine (Cba), cyclopentylalanine, cyclohexylalanine (Cha), and stereoisomers thereof.

19. A compound in accordance with claim 17, wherein said proline analog is selected from the group consisting of hydroxyproline (Hyp), O-benzyl-hydroxyproline (Hyp (Bzl)), homoproline (HoPro), β-homoproline (βHoPro), thiazolidine-4-carboxylic acid (Thz), 1-aminocyclopentane-1-carboxylic acid (Acp), (2S,5R)-5-phenylpyrrolidine-2-carboxylic acid (Ppca), nipecotic acid (Nip), isonipecotic acid (IsoNip), 3-carboxymethyl-1-phenyl-1,3,8-triazospiro [4,5]decan-4-one (Cptd), tetrahydro-isoquinoline-3-carboxylic acid (3-Tic), 3-aminobenzoic acid (3-Abz), and 5H-thiazolo[3,2-a]pyridine-3-carboxylic acid (Btd), and stereoisomers thereof.

20. A compound in accordance with claim 15, wherein said derivatives of lysine (Lys), Orn and Dbu are selected from the group consisting of Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Hly38, Hly27, Hly73, Hly55, Hly28, Hly72, Hly12, Hly123, Hly63, Hly124, Hly82, Hly31, Hly15, Hly125, Hly43, Hly24, Hly5, Hly4, Hly50, Hly81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof.

21. A compound in accordance with claim 15, wherein said negatively charged amino acid is selected from the group consisting of aspartic acid (Asp), glutamic acid (Glu), α-aminohexanedioic acid (Aad), α-aminooctanedioc acid (Asu), homoaspartic acid (HoAsp), γ-carboxy-glutamic acid, 4-carboxyphenylalanine (Phe(4-COOH)), and stereoisomers thereof.

22. A compound in accordance with claim 15, wherein $Y^1$ is selected from the group consisting of Leu, a leucine analog, Lys38, and stereoisomers thereof.

23. A compound in accordance with claim 15, wherein $Y^2$ is selected from the group consisting of Asp, Glu, Aad, and stereoisomers thereof.

24. A compound in accordance with claim 23, wherein $Y^2$ is Aad.

25. A compound in accordance with claim 15, wherein $Y^3$ is selected from the group consisting of Leu, a leucine analog, Phe, a phenylalanine analog, Val, Ile, Ala, Nva, Acpc, Chg, Aib, Abu, Aic, Nal-2, Ana, and stereoisomers thereof.

26. A compound in accordance with claim 15, wherein $Y^4$ is selected from the group consisting of a hydrophobic amino acid, a negatively charged amino acid, and stereoisomers thereof.

27. A compound in accordance with claim 26, wherein said hydrophobic amino acid is selected from the group consisting of Pro, a proline analog, and stereoisomers thereof.

28. A compound in accordance with claim 27, wherein said proline analog is Hyp.

29. A compound in accordance with claim 15, wherein Y is selected from the group consisting of -Nle-Aad-Chg-D-Tyr, -Leu-Aad-Val-Hyp, -Hle-Aad-Phe-Chg, -Lys38-Aad-Leu-D-Pro, -Cpa-Aad-Ile-D-Asp, -Hle-Aad-Aib-D-3-Pal, -Leu-Aad-Ala-Hyp, -Cpa-Asp-Nva-D-Glu, -Cpa-Aad-Aib-D-Thi, -Cpa-Aad-Acpc-Hyp, -Nle-Aad-Val-D-Glu, -Lys38-Aad-Acpc-D-Asp, -Lys38-Aad-D-Phe-D-3-Pal, -Cpa-Aad-Nle-D-Pro, -Lys-Aad-Chg-D-Glu, -Cpa-Aad-Nle-Aad, -Cpa-Aad-Acpc-Aad, -Leu-Aad-Acpc-Aad, -HoPhe-Aad-D-Nal-2-D-Glu, -Lys38-Aad-D-Phe-D-Asp and -Lys38-Aad-D-Phe-D-Val.

30. A compound in accordance with claim 15, wherein Y is selected from the group consisting of -Nle-Glu-Ala-D-Thi, -Cha-Asp-Nle-D-Gln, -Leu-Asp-D-Phe-Aic, -Cpa-Asp-Leu-D-Thi, -HoPhe-Asp-Abu-D-Asn, -Hle-Asp-Acpc-D-Ala, -Leu-Aad-Ana-D-Pro, -Lys38-Asp-Phe(3-Cl)-D-Pro, -Cpa-Asp-Ala-D-Thi, and -HoPhe-Asp-Ala-Hyp.

31. A compound in accordance with claim 1, wherein Y is a tripeptide having the following structure:

$$-Y^1-Y^2-Y^3,$$

wherein
  $Y^1$ is selected from the group consisting of a hydrophobic amino acid and derivatives of lysine, homolysine (Hly), ornithine (Orn) and α,γ-diaminobutyric acid (Dbu);
  $Y^2$ is a negatively charged amino acid;
  $Y^3$ is a hydrophobic amino acid.

32. A compound in accordance with claim 31, wherein $Y^3$ has a carboxyl-terminal group selected from the group consisting of an amide group and a carboxylic acid group.

33. A compound in accordance with claim 31, wherein $Y^1$ is lysine-A38 (Lys38).

34. A compound in accordance with claim 31, wherein $Y^2$ is α-aminohexanedioic acid (Aad).

35. A compound in accordance with claim 31, wherein $Y^3$ is a D-amino acid.

36. A compound in accordance with claim 31, wherein Y is selected from the group consisting of -Lys38-Aad-D-Phe, -Lys38-Aad-Ach, -Lys38-Aad-D-Nal-2, -Lys38-Aad-Ile, -Lys38-Aad-Val, and -Lys38-Aad-Leu.

37. A compound in accordance with claim 31, wherein Y is -Lys38-Aad-Ach.

38. A compound in accordance with claim 31, wherein said compound binds to cells selected from the group consisting of malignant T-cells, malignant B-cells, cancer cells with α1,β2 integrins and multiple myeloma cells.

39. A compound in accordance with claim 38, wherein X is -Nle-Aad-Phg.

40. A method for treating a cancer expressing $\alpha_4\beta_1$-integrin in a subject in need thereof, said method comprising:
   administering to said subject an effective amount of a compound having the formula:

wherein
      the subscripts n, m and q are each independently selected integers of from 0 to 2;
      $R^1$ is selected from the group consisting of hydrogen, halogen, $C_1$-$C_4$ alkyl, $C_1$-$C_4$ alkoxy, and $C_1$-$C_4$ haloalkyl;
      $R^2$ is selected from the group consisting of hydrogen, halogen, $C_1$-$C_4$ alkyl and $C_1$-$C_4$ alkoxy;
      $R^3$ is selected from the group consisting of hydrogen, $C_1$-$C_4$ alkyl and $C_3$-$C_8$ cycloalkyl;
      $R^4$ is H or $CH_3$;
      X is S, O or NH;
      Y is a peptide having r independently selected amino acids, wherein at least one amino acid is selected from the group consisting of an unnatural amino acid and a D-amino acid;
      Z is a chelating agent or a chelating agent-linker conjugate optionally linked to an anticancer agent selected from the group consisting of radionuclides, chemotherapeutic agents, nanoparticles, nanodroplets, liposomal drugs and cytokines; and
      r is an integer of from 3 to 20;
   wherein said effective amount is an amount sufficient for therapeutic benefit or an amount sufficient to target delivery of said anticancer agent.

41. A method in accordance with claim 40, wherein said cancer is a lymphoma or leukemia.

42. A method in accordance with claim 41, wherein said lymphoma or leukemia is selected from the group consisting of non-Hodgkin's lymphoma, Hodgkin's lymphoma, B-cell lymphoma, Burkitt's lymphoma, acute lymphocytic leukemia, chronic lymphocytic leukemia, T-cell lymphoma, multiple myeloma, or hairy cell leukemia.

43. A method in accordance with claim 40, wherein a radionuclide is bound to said chelating agent or chelating agent-linker conjugate.

44. A method for imaging a tumor, organ, or tissue expressing $\alpha_4\beta_1$-integrin, said method comprising:
   (a) administering to a subject in need of such imaging, a compound having formula II(a) or II(b):

wherein
      the subscripts n, m and q are each independently selected integers of from 0 to 2;
      $R^1$ is selected from the group consisting of hydrogen, halogen, $C_1$-$C_4$ alkyl, $C_1$-$C_4$ alkoxy, and $C_1$-$C_4$ haloalkyl;
      $R^2$ is selected from the group consisting of hydrogen, halogen, $C_1$-$C_4$ alkyl and $C_1$-$C_4$ alkoxy;
      $R^3$ is selected from the group consisting of hydrogen, $C_1$-$C_4$ alkyl and $C_3$-$C_8$ cycloalkyl;
      $R^4$ is H or $CH_3$;
      X is S, O or NH;
      Y is a peptide having r independently selected amino acids, wherein at least one amino acid is selected from the group consisting of an unnatural amino acid and a D-amino acid;
      Z is selected from the group consisting of an imaging moiety, a chelating agent or a chelating agent-linker conjugate; and
      r is an integer of from 3 to 20.

45. A method in accordance with claim 44, wherein said imaging moiety is selected from the group consisting of a radionuclide, biotin, a fluorophore, an antibody, horseradish peroxidase, alkaline phosphatase, nanoparticles, quantum dots, nanodroplets of detectable anticancer agents, liposomal drugs and cytokines.

46. A method in accordance with claim 45, wherein said radionuclide is bound to a chelating agent or chelating agent-linker conjugate.

47. A method in accordance with claim 46, wherein radiation from said radionuclide is used to detect said compound, thereby detecting the location of said tumor.

48. A method for treating an inflammatory or autoimmune disease expressing $\alpha_4\beta_1$-integrin in a subject in need thereof, said method comprising:
administering to said subject a therapeutically effective amount of a compound having the formula:

I(a)

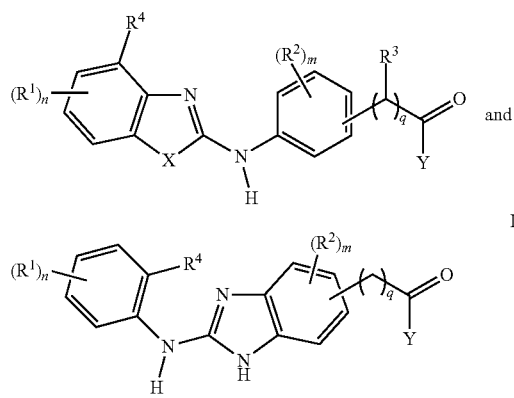

I(b)

and wherein
the subscripts n, m and q are each independently selected integers of from 0 to 2;
$R^1$ is selected from the group consisting of hydrogen, halogen, $C_1$-$C_4$ alkyl, $C_1$-$C_4$ alkoxy, and $C_1$-$C_4$ haloalkyl;
$R^2$ is selected from the group consisting of hydrogen, halogen, $C_1$-$C_4$ alkyl and $C_1$-$C_4$ alkoxy;
$R^3$ is selected from the group consisting of hydrogen, $C_1$-$C_4$ alkyl and $C_3$-$C_8$ cycloalkyl;
$R^4$ is H or $CH_3$;
X is S, O or NH;
Y is a peptide having r independently selected amino acids, wherein at least one amino acid is selected from the group consisting of an unnatural amino acid and a D-amino acid; and
r is an integer of from 3 to 20.

49. A targeting conjugate having a formula selected from the group consisting of:

II(a)

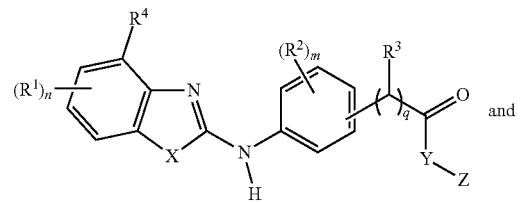

and

II(b)

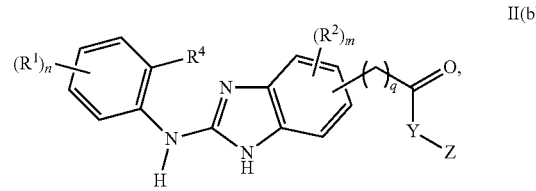

wherein
the subscripts n, m and q are each independently selected integers of from 0 to 2;
$R^1$ is selected from the group consisting of hydrogen, halogen, $C_1$-$C_4$ alkyl, $C_1$-$C_4$ alkoxy, and $C_1$-$C_4$ haloalkyl;
$R^2$ is selected from the group consisting of hydrogen, halogen, $C_1$-$C_4$ alkyl and $C_1$-$C_4$ alkoxy;
$R^3$ is selected from the group consisting of hydrogen, $C_1$-$C_4$ alkyl and $C_3$-$C_8$ cycloalkyl;
$R^4$ is H or $CH_3$;
X is S, O or NH;
Y is a peptide having r independently selected amino acids, wherein at least one amino acid is selected from the group consisting of an unnatural amino acid and a D-amino acid;
Z is a chelating agent or a chelating agent-linker conjugate; and
r is an integer of from 3 to 20; and wherein said targeting conjugate binds to $\alpha_4\beta_1$ integrin with a binding constant of less than 10 micromolar.

* * * * *